(12) United States Patent
Ling et al.

(10) Patent No.: US 12,188,039 B2
(45) Date of Patent: Jan. 7, 2025

(54) RECOMBINANT ADENO-ASSOCIATED VIRAL VECTOR FOR GENE DELIVERY

(71) Applicant: THE BOARD OF REGENTS OF THE UNIVERSITY OF TEXAS SYSTEM, Austin, TX (US)

(72) Inventors: Qinglan Ling, Dallas, TX (US); Steven J Gray, Southlake, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 490 days.

(21) Appl. No.: 17/092,239

(22) Filed: Nov. 7, 2020

(65) Prior Publication Data

US 2021/0139933 A1     May 13, 2021

Related U.S. Application Data

(60) Provisional application No. 62/932,828, filed on Nov. 8, 2019.

(51) Int. Cl.
*A61K 48/00* (2006.01)
*A61P 43/00* (2006.01)
*C12N 15/86* (2006.01)

(52) U.S. Cl.
CPC .............. *C12N 15/86* (2013.01); *A61P 43/00* (2018.01); *C12N 2750/14141* (2013.01)

(58) Field of Classification Search
CPC .. A61K 48/00; A61K 48/005; A61K 48/0075; C12N 15/86; C12N 2740/14141; C12N 2750/14143; C12N 2800/22; C12N 2830/50

See application file for complete search history.

(56) References Cited

U.S. PATENT DOCUMENTS

| 10,016,514 | B2* | 7/2018 | Keimel ............... A61K 35/761 |
| 2007/0105114 | A1 | 5/2007 | Li et al. |
| 2014/0196176 | A1* | 7/2014 | Heintz ............... C12N 15/1003 536/25.4 |
| 2016/0331846 | A1 | 11/2016 | Keimel et al. |
| 2018/0265893 | A1* | 9/2018 | Mallol Dominguez ..................... C12N 15/86 |
| 2019/0241633 | A1 | 8/2019 | Fotin-Mleczek et al. |

(Continued)

FOREIGN PATENT DOCUMENTS

| WO | WO 16/115632 | * 7/2016 |
| WO | 2016187053 A1 | 11/2016 |

(Continued)

OTHER PUBLICATIONS

Ling et al, Adeno-associated viral vector serotype 9-based gene replacement therapy for SURF1-related Leigh syndrome, Molecular Therapy: Methods & Clinical Development 23: 158-168, 2021.*

(Continued)

*Primary Examiner* — Kevin K Hill
(74) *Attorney, Agent, or Firm* — DLA Piper LLP US

(57) ABSTRACT

The present disclosure provides methods and compositions for the treatment of diseases and genetic disorders linked to SURF1 loss and/or misfunction. The methods and compositions of the present disclosure comprise rAAV vectors and rAAV viral vectors comprising transgene nucleic acid molecules comprising nucleic acid sequences encoding for a SURF1 polypeptide.

18 Claims, 5 Drawing Sheets

Specification includes a Sequence Listing.

(56) References Cited

U.S. PATENT DOCUMENTS

| | | |
|---|---|---|
| 2021/0107948 A1 | 4/2021 | Richard et al. |
| 2021/0330811 A1 | 10/2021 | Gray et al. |
| 2022/0228167 A1 | 7/2022 | Ronzitti et al. |

FOREIGN PATENT DOCUMENTS

| | | | |
|---|---|---|---|
| WO | WO 17/218450 | * | 12/2017 |
| WO | 2019094061 A1 | | 5/2019 |
| WO | 2019193119 A1 | | 10/2019 |
| WO | 2020200499 A1 | | 10/2020 |

OTHER PUBLICATIONS

Karumuthil-Melethil et al, Intrathecal Administration of AAV/GALC Vectors in 10-11-Day-Old Twitcher Mice Improves Survival and Is Enhanced by Bone Marrow Transplant, J. Neurosci. Res. 94: 1138-1151, 2016.*

Bailey et al, Development of Intrathecal AAV9 Gene Therapy for Giant Axonal Neuropathy, Molecular Therapy: Methods & Clinical Development 9: 160-171, Jun. 2018.*

Bradbury et al, Abstract 397. CNS-Directed AAV9 Gene Therapy for the Treatment of Canine Globoid Cell Leukodystrophy (Krabbe Disease), Molecular Therapy 27(4) Suppl 1: p. 189, Apr. 2019.*

Saade et al, Abstract 399. Review of Safety and Interim Analysis of Efficacy of a First-in-Human Intrathecal Gene Transfer Study for Giant Axonal Neuropathy, Molecular Therapy 27(4) Suppl 1: p. 190, Apr. 2019.*

Bharucha-Goebel et al, Abstract 637. Immune Analysis Following Intrathecal Gene Transfer: 3-Year Data from Clinical Intrathecal Gene Transfer Trial for Patients with Giant Axonal Neuropathy, Molecular Therapy 27(4) Suppl 1: p. 298, Apr. 2019.*

Snyder et al, Comparison of Adeno-Associated Viral Vector Serotypes for Spinal Cord and Motor Neuron Gene Delivery, Human Gene Therapy 22: 1129-1135, 2011.*

Dominguez et al, Intravenous scAAV9 delivery of a codon-optimized SMN1 sequence rescues SMA mice, Human Molecular Genetics 20(4): 681-693, 2011.*

Tiranti et al, Loss-of-Function Mutations of SURF-1 Are Specifically Associated with Leigh Syndrome with Cytochrome c Oxidase Deficiency, Ann. Neurol. 46: 161-166, 1999.*

Kingdoms of Life, waynesword.palomar.edu/trfeb98.htm, last visited Apr. 8, 2021.*

Mammal, en.wikipedia.org/wiki/Mammal, last visited Aug. 31, 2022.*

Mingozzi and High, Immune responses to AAV vectors: overcoming barriers to successful gene therapy, Blood 122(1): 23-36, 2013.*

Kattenhorn et al, Adeno-Associated Virus Gene Therapy for Liver Disease, Human Gene Therapy 27(12): 947-961, Nov. 28, 2016.*

Inak et al, SURF1 mutations causative of Leigh syndrome impair human neurogenesis, bioRxiv, 32 pages, doi.org/10.1101/551390; available online Feb. 20, 2019.*

Fumoto et al, Targeted Gene Delivery: Importance of Administration Routes, INTECH, Novel Gene Therapy Approaches, p. 3-31; editors Wei and Good, publisher Books on Demand, 2013.*

Daya et al, Gene Therapy Using Adeno-Associated Virus Vectors, Clin. Microbiol. Rev. 21(4): 583-593, 2008.*

Perrin, Make Mouse Studies Work, Nature (507): 423-425, 2014.*

Di Meo et al, AAV9-based gene therapy partially ameliorates the clinical phenotype of a mouse model of Leigh syndrome, Gene Therapy 24: 661-667, 2017.*

Chen et al, Management of Leigh syndrome: Current status and new insights, Clinical Genetics 93: 1131-1140, Jun. 2018; available online Sep. 14, 2017.*

GenBank AY414057, human SURF1 gene, 2013.*

GenBank Q15526, human SURF1, amino acid sequence, Nov. 22, 2017.*

Lake et al, Leigh Syndrome: One Disorder, More Than 75 Monogenic Causes, Ann. Neurol. 79: 190-203, 2016.*

Saraiva et al, Gene therapy for the CNS using AAVs: The impact of systemic delivery by AAV9, J. Controlled Release 241: 94-109, 2016.*

Grote et al, JCat: a novel tool to adapt codon usage of a target gene to its potential expression host, Nucleic Acids Research 33: W526-W531; doi: 10.1093/nar/gki376, 2005.*

Daniel et al, ATGme: Open-source web application for rare codon identification and custom DNA sequence optimization, BMC Bioinformatics 16: 303, 6 pages, doi. 10.1186/s12859-015-0743-5; 2015.*

PCT International Application No. PCT/US20/59570, International Search Report of the International Searching Authority, dated Feb. 17, 2021, 5 pages.

PCT International Application No. PCT/US20/59570, Written Opinion of the International Searching Authority, dated Feb. 17, 2021, 9 pages.

Extended European Search Report issued in application No. EP20885638, 12 pages, dated Nov. 2, 2023.

Database Uniprot [Online] Uniprot; Nov. 1996 (Nov. 1, 1996), Lennard A: "RecName: Full=Surfeit locus protein 1;", XP093094107, retrieved from EBI accession No. Q15526 Database accession No. Q15526 *abstract; sequence*.

Database EMBL [Online] EMBL; Jan. 15, 2018 (Jan. 15, 2018), Kozhevnikova E N et al: "Cloning vector pCMV-CBA-Cas9-Rosa26gRNAs, complete sequence.", XP093094237, retrieved from EBI accession No. MG550105 Database accession No. MG550105 *abstract; sequence*.

\* cited by examiner

SEQUENCE LISTING

```
<160> NUMBER OF SEQ ID NOS: 21

<210> SEQ ID NO 1
<211> LENGTH: 299
<212> TYPE: PRT
<213> ORGANISM: Homo sapiens

<400> SEQUENCE: 1

Ala Ala Val Ala Ala Leu Gln Leu Gly Leu Arg Ala Ala Gly Leu Gly
1               5                   10                  15

Arg Ala Pro Ala Ser Ala Ala Trp Arg Ser Val Leu Arg Val Ser Pro
```

```
                20                  25                  30
Arg Pro Gly Val Ala Trp Arg Pro Ser Arg Cys Gly Ser Ser Ala Ala
            35                  40                  45

Glu Ala Ser Ala Thr Lys Ala Glu Asp Asp Ser Phe Leu Gln Trp Val
        50                  55                  60

Leu Leu Leu Ile Pro Val Thr Ala Phe Gly Leu Gly Thr Trp Gln Val
65                  70                  75                  80

Gln Arg Arg Lys Trp Lys Leu Asn Leu Ile Ala Glu Leu Glu Ser Arg
                85                  90                  95

Val Leu Ala Glu Pro Val Pro Leu Pro Ala Asp Pro Met Glu Leu Lys
            100                 105                 110

Asn Leu Glu Tyr Arg Pro Val Lys Val Arg Gly Cys Phe Asp His Ser
        115                 120                 125

Lys Glu Leu Tyr Met Met Pro Arg Thr Met Val Asp Pro Val Arg Glu
    130                 135                 140

Ala Arg Glu Gly Gly Leu Ile Ser Ser Ser Thr Gln Ser Gly Ala Tyr
145                 150                 155                 160

Val Val Thr Pro Phe His Cys Thr Asp Leu Gly Val Thr Ile Leu Val
                165                 170                 175

Asn Arg Gly Phe Val Pro Arg Lys Lys Val Asn Pro Glu Thr Arg Gln
            180                 185                 190

Lys Gly Gln Ile Glu Gly Glu Val Asp Leu Ile Gly Met Val Arg Leu
        195                 200                 205

Thr Glu Thr Arg Gln Pro Phe Val Pro Glu Asn Asn Pro Glu Arg Asn
    210                 215                 220

His Trp His Tyr Arg Asp Leu Glu Ala Met Ala Arg Ile Thr Gly Ala
225                 230                 235                 240

Glu Pro Ile Phe Ile Asp Ala Asn Phe Gln Ser Thr Val Pro Gly Gly
                245                 250                 255

Pro Ile Gly Gly Gln Thr Arg Val Thr Leu Arg Asn Glu His Leu Gln
            260                 265                 270

Tyr Ile Val Thr Trp Tyr Gly Leu Ser Ala Ala Thr Ser Tyr Leu Trp
        275                 280                 285

Phe Lys Lys Phe Leu Arg Gly Thr Pro Gly Val
    290                 295

<210> SEQ ID NO 2
<211> LENGTH: 300
<212> TYPE: PRT
<213> ORGANISM: Homo sapiens

<400> SEQUENCE: 2

Met Ala Ala Val Ala Ala Leu Gln Leu Gly Leu Arg Ala Ala Gly Leu
1               5                   10                  15

Gly Arg Ala Pro Ala Ser Ala Ala Trp Arg Ser Val Leu Arg Val Ser
            20                  25                  30

Pro Arg Pro Gly Val Ala Trp Arg Pro Ser Arg Cys Gly Ser Ser Ala
        35                  40                  45

Ala Glu Ala Ser Ala Thr Lys Ala Glu Asp Asp Ser Phe Leu Gln Trp
    50                  55                  60

Val Leu Leu Leu Ile Pro Val Thr Ala Phe Gly Leu Gly Thr Trp Gln
65                  70                  75                  80

Val Gln Arg Arg Lys Trp Lys Leu Asn Leu Ile Ala Glu Leu Glu Ser
                85                  90                  95
```

Arg Val Leu Ala Glu Pro Val Pro Leu Pro Ala Asp Pro Met Glu Leu
                100                 105                 110

Lys Asn Leu Glu Tyr Arg Pro Val Lys Val Arg Gly Cys Phe Asp His
        115                 120                 125

Ser Lys Glu Leu Tyr Met Met Pro Arg Thr Met Val Asp Pro Val Arg
130                 135                 140

Glu Ala Arg Glu Gly Gly Leu Ile Ser Ser Thr Gln Ser Gly Ala
145                 150                 155                 160

Tyr Val Val Thr Pro Phe His Cys Thr Asp Leu Gly Val Thr Ile Leu
                165                 170                 175

Val Asn Arg Gly Phe Val Pro Arg Lys Lys Val Asn Pro Glu Thr Arg
        180                 185                 190

Gln Lys Gly Gln Ile Glu Gly Glu Val Asp Leu Ile Gly Met Val Arg
        195                 200                 205

Leu Thr Glu Thr Arg Gln Pro Phe Val Pro Glu Asn Asn Pro Glu Arg
210                 215                 220

Asn His Trp His Tyr Arg Asp Leu Glu Ala Met Ala Arg Ile Thr Gly
225                 230                 235                 240

Ala Glu Pro Ile Phe Ile Asp Ala Asn Phe Gln Ser Thr Val Pro Gly
                245                 250                 255

Gly Pro Ile Gly Gly Gln Thr Arg Val Thr Leu Arg Asn Glu His Leu
        260                 265                 270

Gln Tyr Ile Val Thr Trp Tyr Gly Leu Ser Ala Ala Thr Ser Tyr Leu
        275                 280                 285

Trp Phe Lys Lys Phe Leu Arg Gly Thr Pro Gly Val
290                 295                 300

<210> SEQ ID NO 3
<211> LENGTH: 897
<212> TYPE: DNA
<213> ORGANISM: Homo sapiens

<400> SEQUENCE: 3
gccgctgtgg ctgcactcca actcggcctg agagccgcag gactgggcag agcaccggca      60
tcagccgcct ggagaagcgt gctcagagtg tccccaaggc ccggagtggc atggcgccca     120
tcgagatgcg gcagctcagc tgcggaagcc tccgcgacca aggccgaaga tgactccttc     180
ctgcaatggg tgctgctgct gattcccgtg accgctttcg ggctggggac ttggcaagtg     240
cagcggcgca agtggaagct gaacctgatt gccgagctgg agtctcgcgt gctggcggaa     300
cctgtgccgt tgcctgccga tccgatggag ctgaagaacc tggagtaccg gcccgtgaag     360
gtccgaggct gcttcgacca ttccaaggaa ctctacatga tgccacgcac gatggtggac     420
cctgtgcggg aagctcgcga aggggtctg atttcgagct ccacccagtc gggagcctat     480
gtcgtcaccc cttttcactg taccgacctc ggcgtcacaa tccttgtgaa tcggggattc     540
gtgcctcgca agaaagtcaa cccggaaacc cggcagaagg acagatcga gggcgaagtg     600 gatctgatcg gcatggtccg gctcaccgag actcggcagc cgtttgtgcc cgagaacaac     660
cccgagcgga accactggca ctaccgggac ctggaagcca tggccaggat cactggtgcc     720
gagccgattt tcatcgacgc gaacttccag tccactgtcc ctgggggacc catcggtgga     780
cagacccgcg tgaccctgag gaacgaacac ttgcagtaca tcgtgacttg gtacggactt     840
tccgccgcca cctcctacct ctggttcaaa aagttcctga ggggtactcc gggagtg      897

<210> SEQ ID NO 4

<211> LENGTH: 900
<212> TYPE: DNA
<213> ORGANISM: Homo sapiens

<400> SEQUENCE: 4

| | | | | | | |
|---|---|---|---|---|---|---|
| gccgctgtgg | ctgcactcca | actcggcctg | agagccgcag | gactgggcag | agcaccggca | 60 |
| tcagccgcct | ggagaagcgt | gctcagagtg | tccccaaggc | ccggagtggc | atggcgccca | 120 |
| tcgagatgcg | gcagctcagc | tgcggaagcc | tccgcgacca | aggccgaaga | tgactccttc | 180 |
| ctgcaatggg | tgctgctgct | gattcccgtg | accgctttcg | ggctggggac | ttggcaagtg | 240 |
| cagcggcgca | agtggaagct | gaacctgatt | gccgagctgg | agtctcgcgt | gctggcggaa | 300 |
| cctgtgccgt | tgcctgccga | tccgatggag | ctgaagaacc | tggagtaccg | gcccgtgaag | 360 |
| gtccgaggct | gcttcgacca | ttccaaggaa | ctctacatga | tgccacgcac | gatggtggac | 420 |
| cctgtgcggg | aagctcgcga | aggggtctg | atttcgagct | ccacccagtc | gggagcctat | 480 |
| gtcgtcaccc | cttttcactg | taccgacctc | ggcgtcacaa | tccttgtgaa | tcggggattc | 540 |
| gtgcctcgca | agaaagtcaa | cccggaaacc | cggcagaagg | gacagatcga | gggcgaagtg | 600 |
| gatctgatcg | gcatggtccg | gctcaccgag | actcggcagc | cgtttgtgcc | cgagaacaac | 660 |
| cccgagcgga | accactggca | ctaccgggac | ctggaagcca | tggccaggat | cactggtgcc | 720 |
| gagccgattt | tcatcgacgc | gaacttccag | tccactgtcc | ctgggggacc | catcggtgga | 780 |
| cagacccgcg | tgaccctgag | gaacgaacac | ttgcagtaca | tcgtgacttg | gtacggactt | 840 |
| tccgccgcca | cctcctacct | ctggttcaaa | aagttcctga | ggggtactcc | gggagtgtga | 900 |

<210> SEQ ID NO 5
<211> LENGTH: 903
<212> TYPE: DNA
<213> ORGANISM: Homo sapiens

<400> SEQUENCE: 5

| | | | | | | |
|---|---|---|---|---|---|---|
| gccgctgtgg | ctgcactcca | actcggcctg | agagccgcag | gactgggcag | agcaccggca | 60 |
| tcagccgcct | ggagaagcgt | gctcagagtg | tccccaaggc | ccggagtggc | atggcgccca | 120 |
| tcgagatgcg | gcagctcagc | tgcggaagcc | tccgcgacca | aggccgaaga | tgactccttc | 180 |
| ctgcaatggg | tgctgctgct | gattcccgtg | accgctttcg | ggctggggac | ttggcaagtg | 240 |
| cagcggcgca | agtggaagct | gaacctgatt | gccgagctgg | agtctcgcgt | gctggcggaa | 300 |
| cctgtgccgt | tgcctgccga | tccgatggag | ctgaagaacc | tggagtaccg | gcccgtgaag | 360 |
| gtccgaggct | gcttcgacca | ttccaaggaa | ctctacatga | tgccacgcac | gatggtggac | 420 |
| cctgtgcggg | aagctcgcga | aggggtctg | atttcgagct | ccacccagtc | gggagcctat | 480 |
| gtcgtcaccc | cttttcactg | taccgacctc | ggcgtcacaa | tccttgtgaa | tcggggattc | 540 |
| gtgcctcgca | agaaagtcaa | cccggaaacc | cggcagaagg | gacagatcga | gggcgaagtg | 600 |
| gatctgatcg | gcatggtccg | gctcaccgag | actcggcagc | cgtttgtgcc | cgagaacaac | 660 |
| cccgagcgga | accactggca | ctaccgggac | ctggaagcca | tggccaggat | cactggtgcc | 720 |
| gagccgattt | tcatcgacgc | gaacttccag | tccactgtcc | ctgggggacc | catcggtgga | 780 |
| cagacccgcg | tgaccctgag | gaacgaacac | ttgcagtaca | tcgtgacttg | gtacggactt | 840 |
| tccgccgcca | cctcctacct | ctggttcaaa | aagttcctga | ggggtactcc | gggagtgtga | 900 |
| taa | | | | | | 903 |

<210> SEQ ID NO 6
<211> LENGTH: 907

<212> TYPE: DNA
<213> ORGANISM: Homo sapiens

<400> SEQUENCE: 6

```
caccgccgct gtggctgcac tccaactcgg cctgagagcc gcaggactgg gcagagcacc    60
ggcatcagcc gcctggagaa gcgtgctcag agtgtcccca aggcccggag tggcatggcg   120
cccatcgaga tgcggcagct cagctgcgga agcctccgcg accaaggccg aagatgactc   180
cttcctgcaa tgggtgctgc tgctgattcc cgtgaccgct tcgggctggg gacttggca   240
agtgcagcgg cgcaagtgga agctgaacct gattgccgag ctggagtctc gcgtgctggc   300
ggaacctgtg ccgttgcctg ccgatccgat ggagctgaag aacctggagt accggcccgt   360
gaaggtccga ggctgcttcg accattccaa ggaactctac atgatgccac gcacgatggt   420
ggaccctgtg cgggaagctc gcgaaggggg tctgatttcg agctccaccc agtcgggagc   480
ctatgtcgtc accccttttc actgtaccga cctcggcgtc acaatccttg tgaatcgggg   540
attcgtgcct cgcaagaaag tcaacccgga aacccggcag aagggacaga tcgagggcga   600
agtggatctg atcggcatgg tccggctcac cgagactcgg cagccgtttg tgcccgagaa   660
caaccccgag cggaaccact ggcactaccg ggacctggaa gccatggcca ggatcactgg   720
tgccgagccg attttcatcg acgcgaactt ccagtccact gtccctgggg gacccatcgg   780
tggacagacc cgcgtgaccc tgaggaacga acacttgcag tacatcgtga cttggtacgg   840
actttccgcc gccacctcct acctctggtt caaaaagttc ctgaggggta ctccgggagt   900
gtgataa                                                             907
```

<210> SEQ ID NO 7
<211> LENGTH: 900
<212> TYPE: DNA
<213> ORGANISM: Homo sapiens

<400> SEQUENCE: 7

```
atggccgctg tggctgcact ccaactcggc ctgagagccg caggactggg cagagcaccg    60
gcatcagccg cctggagaag cgtgctcaga gtgtccccaa ggcccggagt ggcatggcgc   120
ccatcgagat gcggcagctc agctgcggaa gcctccgcga ccaaggccga agatgactcc   180
ttcctgcaat gggtgctgct gctgattccc gtgaccgctt cgggctgggg acttggcaa   240
gtgcagcggc gcaagtggaa gctgaacctg attgccgagc tggagtctcg cgtgctggcg   300
gaacctgtgc cgttgcctgc cgatccgatg gagctgaaga acctggagta ccggcccgtg   360
aaggtccgag gctgcttcga ccattccaag gaactctaca tgatgccacg cacgatggtg   420
gaccctgtgc gggaagctcg cgaagggggt ctgatttcga gctccaccca gtcgggagcc   480
tatgtcgtca ccccttttca ctgtaccgac ctcggcgtca caatccttgt gaatcgggga   540
ttcgtgcctc gcaagaaagt caacccggaa acccggcaga agggacagat cgagggcgaa   600
gtggatctga tcggcatggt ccggctcacc gagactcggc agccgtttgt gcccgagaac   660
aaccccgagc ggaaccactg gcactaccgg gacctggaag ccatggccag gatcactggt   720
gccgagccga ttttcatcga cgcgaacttc cagtccactg tccctggggg acccatcggt   780
ggacagaccc gcgtgaccct gaggaacgaa cacttgcagt acatcgtgac ttggtacgga   840
ctttccgccg ccacctccta cctctggttc aaaaagttcc tgagggtac tccgggagtg   900
```

<210> SEQ ID NO 8
<211> LENGTH: 903
<212> TYPE: DNA

<213> ORGANISM: Homo sapiens

<400> SEQUENCE: 8

| | | | | | |
|---|---|---|---|---|---|
| atggccgctg | tggctgcact | ccaactcggc | ctgagagccg | caggactggg | cagagcaccg | 60 |
| gcatcagccg | cctggagaag | cgtgctcaga | gtgtccccaa | ggcccggagt | ggcatggcgc | 120 |
| ccatcgagat | gcggcagctc | agctgcggaa | gcctccgcga | ccaaggccga | agatgactcc | 180 |
| ttcctgcaat | gggtgctgct | gctgattccc | gtgaccgctt | cgggctggg | gacttggcaa | 240 |
| gtgcagcggc | gcaagtggaa | gctgaacctg | attgccgagc | tggagtctcg | cgtgctggcg | 300 |
| gaacctgtgc | cgttgcctgc | cgatccgatg | gagctgaaga | acctggagta | ccggcccgtg | 360 |
| aaggtccgag | gctgcttcga | ccattccaag | gaactctaca | tgatgccacg | cacgatggtg | 420 |
| gaccctgtgc | gggaagctcg | cgaaggggt | ctgatttcga | gctccaccca | gtcgggagcc | 480 |
| tatgtcgtca | ccccttttca | ctgtaccgac | ctcggcgtca | caatccttgt | gaatcgggga | 540 |
| ttcgtgcctc | gcaagaaagt | caacccgaaa | accggcaga | agggacagat | cgagggcgaa | 600 |
| gtggatctga | tcggcatggt | ccggctcacc | gagactcggc | agccgtttgt | gcccgagaac | 660 |
| aaccccgagc | ggaaccactg | gcactaccgg | gacctggaag | ccatggccag | gatcactggt | 720 |
| gccgagccga | tttcatcga | cgcgaacttc | cagtccactg | tccctggggg | acccatcggt | 780 |
| ggacagaccc | gcgtgaccct | gaggaacgaa | cacttgcagt | acatcgtgac | ttggtacgga | 840 |
| cttccgccg | ccacctccta | cctctggttc | aaaaagttcc | tgaggggtac | tccgggagtg | 900 |
| tga | | | | | | 903 |

<210> SEQ ID NO 9
<211> LENGTH: 906
<212> TYPE: DNA
<213> ORGANISM: Homo sapiens

<400> SEQUENCE: 9

| | | | | | |
|---|---|---|---|---|---|
| atggccgctg | tggctgcact | ccaactcggc | ctgagagccg | caggactggg | cagagcaccg | 60 |
| gcatcagccg | cctggagaag | cgtgctcaga | gtgtccccaa | ggcccggagt | ggcatggcgc | 120 |
| ccatcgagat | gcggcagctc | agctgcggaa | gcctccgcga | ccaaggccga | agatgactcc | 180 |
| ttcctgcaat | gggtgctgct | gctgattccc | gtgaccgctt | tcgggctggg | gacttggcaa | 240 |
| gtgcagcggc | gcaagtggaa | gctgaacctg | attgccgagc | tggagtctcg | cgtgctggcg | 300 |
| gaacctgtgc | cgttgcctgc | cgatccgatg | gagctgaaga | acctggagta | ccggcccgtg | 360 |
| aaggtccgag | gctgcttcga | ccattccaag | gaactctaca | tgatgccacg | cacgatggtg | 420 |
| gaccctgtgc | gggaagctcg | cgaaggggt | ctgatttcga | gctccaccca | gtcgggagcc | 480 |
| tatgtcgtca | ccccttttca | ctgtaccgac | ctcggcgtca | caatccttgt | gaatcgggga | 540 |
| ttcgtgcctc | gcaagaaagt | caacccggaa | accggcaga | agggacagat | cgagggcgaa | 600 |
| gtggatctga | tcggcatggt | ccggctcacc | gagactcggc | agccgtttgt | gcccgagaac | 660 |
| aaccccgagc | ggaaccactg | gcactaccgg | gacctggaag | ccatggccag | gatcactggt | 720 |
| gccgagccga | tttcatcga | cgcgaacttc | cagtccactg | tccctggggg | acccatcggt | 780 |
| ggacagaccc | gcgtgaccct | gaggaacgaa | cacttgcagt | acatcgtgac | ttggtacgga | 840 |
| cttccgccg | ccacctccta | cctctggttc | aaaaagttcc | tgaggggtac | tccgggagtg | 900 |
| tgataa | | | | | | 906 |

<210> SEQ ID NO 10
<211> LENGTH: 910

```
<212> TYPE: DNA
<213> ORGANISM: Homo sapiens

<400> SEQUENCE: 10
caccatggcc gctgtggctg cactccaact cggcctgaga gccgcaggac tgggcagagc      60
accggcatca gccgcctgga gaagcgtgct cagagtgtcc ccaaggcccg gagtggcatg     120
gcgcccatcg agatgcggca gctcagctgc ggaagcctcc gcgaccaagg ccgaagatga     180
ctccttcctg caatgggtgc tgctgctgat tcccgtgacc gctttcgggc tggggacttg     240
gcaagtgcag cggcgcaagt ggaagctgaa cctgattgcc gagctggagt ctcgcgtgct     300
ggcggaacct gtgccgttgc ctgccgatcc gatggagctg aagaacctgg agtaccggcc     360
cgtgaaggtc cgaggctgct tcgaccattc caaggaactc tacatgatgc cacgcacgat     420
ggtggacccc tgtgcgggaag ctcgcgaagg gggtctgatt tcgagctcca cccagtcggg     480
agcctatgtc gtcaccccct ttcactgtac cgacctcggc gtcacaatcc ttgtgaatcg     540
gggattcgtg cctcgcaaga aagtcaaccc ggaaacccgg cagaagggac agatcgaggg     600
cgaagtggat ctgatcggca tggtccggct caccgagact cggcagccgt tgtgcccga      660
gaacaaccccc gagcggaacc actggcacta ccgggacctg gaagccatgg ccaggatcac     720
tggtgccgag ccgattttca tcgacgcgaa cttccagtcc actgtccctg ggggacccat     780
cggtggacag acccgcgtga ccctgaggaa cgaacacttg cagtacatcg tgacttggta     840
cggactttcc gccgccacct cctacctctg gttcaaaaag ttcctgaggg gtactccggg     900
agtgtgataa                                                            910

<210> SEQ ID NO 11
<211> LENGTH: 1092
<212> TYPE: DNA
<213> ORGANISM: Homo sapiens

<400> SEQUENCE: 11
ctgcgtcccg gaagcgcccg cggggccggg tgcgatggcg gcggtggctg cgttgcagct      60
ggggctgcgg gcggcggggc tgggacgggc cccggccagc gccgcctgga ggagcgtcct     120
cagggtctcc ccgcgcccag gggtggcctg gaggccaagc agatgtggca gttctgcagc     180
agaagcatct gccacaaaag cggaagatga ctcctttctt cagtgggtcc tgctcctcat     240
ccctgtgact gcctttggct gggggacatg gcaggtccag cgtcggaagt ggaagctgaa     300
cctgattgca gagttggagt ccagagttct ggctgagcct gtccctctgc agccgacccc     360
aatgaaactg aaaaatctgg agtataggcc agtgaaggtc aggggggtgct ttgaccattc     420
caaggagctg tatatgatgc cccggaccat ggtggaccct gtccgggagg cccgggaggg     480
cggcctcatc tcctcctcaa ctcagagtgg ggcctatgtg gtcactccct tccactgcac     540
cgacctggga gtcaccatcc tggtaaatag agggttcgtt cccaggaaga aagtgaatcc     600
tgaaacccgg cagaaaggcc agattgaggg agaagtggac ctcattggga tggtgaggct     660
gacagaaacc aggcagccct tgtccctga gaacaatcca gaaggaacc actggcatta     720
tcgagacctg gaagctatgg ccagaatcac aggcgcagag cccatcttca ttgatgccaa     780
cttccagagc acagtccctg gaggacccat ggagggcaa accagagtta ctctgaggaa     840
cgagcatctg cagtacatcg tgacctggta tggactctct gcagctacat cctacctgtg     900
gtttaagaaa ttcctacgtg ggacacctgg tgtgtgacag atcagctgct gaagccctgt     960
ccctggataa tgcagtattt caagactgcc tttatgctgg atcatgtgct actggtataa    1020
```

```
agttctggcc ttctacctta aatgagctca tgactggttc atcataaaat cctggcttgg   1080
tttcagtcca aa                                                       1092

<210> SEQ ID NO 12
<211> LENGTH: 169
<212> TYPE: DNA
<213> ORGANISM: adeno-associated virus

<400> SEQUENCE: 12
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag ctggcgtaat agcgaagagg cccgcaccga tcgcccttc               169

<210> SEQ ID NO 13
<211> LENGTH: 106
<212> TYPE: DNA
<213> ORGANISM: Adeno-Associated Virus

<400> SEQUENCE: 13
ctgcgcgctc gctcgctcac tgaggccgcc cgggcaaagc ccgggcgtcg ggcgaccttt    60
ggtcgcccgg cctcagtgag cgagcgagcg cgcagagagg gagtgg                  106

<210> SEQ ID NO 14
<211> LENGTH: 164
<212> TYPE: DNA
<213> ORGANISM: Artificial Sequence
<220> FEATURE:
<223> OTHER INFORMATION: JeT promoter

<400> SEQUENCE: 14
gggcggagtt agggcggagc caatcagcgt gcgccgttcc gaaagttgcc ttttatggct    60
gggcggagaa tgggcggtga acgccgatga ttatataagg acgcgccggg tgtggcacag   120
ctagttccgt cgcagccggg atttgggtcg cggttcttgt ttgt                    164

<210> SEQ ID NO 15
<211> LENGTH: 225
<212> TYPE: DNA
<213> ORGANISM: Homo sapiens

<400> SEQUENCE: 15
caattgaggg cgtcaccgct aaggctccgc cccagcctgg gctccacaac caatgaaggg    60
taatctcgac aaagagcaag gggtggggcg cgggcgcgca ggtgcagcag cacacaggct   120
ggtcgggagg gcggggcgcg acgtctgccg tgcggggtcc cggcatcggt tgcgcgcgcg   180
ctccctcctc tcggagagag ggctgtggta aacccgtcc ggaaa                    225

<210> SEQ ID NO 16
<211> LENGTH: 123
<212> TYPE: DNA
<213> ORGANISM: Simian virus 40

<400> SEQUENCE: 16
tgtttattgc agcttataat ggttacaaat aaagcaatag catcacaaat ttcacaaata    60
aagcattttt ttcactgcat tctagttgtg gtttgtccaa actcatcaat gtatcttatc   120
atg                                                                 123

<210> SEQ ID NO 17
<211> LENGTH: 589
```

<212> TYPE: DNA
<213> ORGANISM: Artificial Sequence
<220> FEATURE:
<223> OTHER INFORMATION: pUC19 origin of replication

<400> SEQUENCE: 17

| | | | | | |
|---|---|---|---|---|---|
| ttgagatcct | ttttttctgc | gcgtaatctg | ctgcttgcaa | acaaaaaaac | caccgctacc | 60 |
| agcggtggtt | tgtttgccgg | atcaagagct | accaactctt | tttccgaagg | taactggctt | 120 |
| cagcagagcg | cagataccaa | atactgttct | tctagtgtag | ccgtagttag | gccaccactt | 180 |
| caagaactct | gtagcaccgc | ctacatacct | cgctctgcta | atcctgttac | cagtggctgc | 240 |
| tgccagtggc | gataagtcgt | gtcttaccgg | gttggactca | agacgatagt | taccggataa | 300 |
| ggcgcagcgg | tcgggctgaa | cggggggttc | gtgcacacag | cccagcttgg | agcgaacgac | 360 |
| ctacaccgaa | ctgagatacc | tacagcgtga | gctatgagaa | agcgccacgc | ttcccgaagg | 420 |
| gagaaaggcg | gacaggtatc | cggtaagcgg | cagggtcgga | acaggagagc | gcacgaggga | 480 |
| gcttccaggg | ggaaacgcct | ggtatcttta | tagtcctgtc | gggtttcgcc | acctctgact | 540 |
| tgagcgtcga | ttttttgtgat | gctcgtcagg | ggggcggagc | ctatggaaa | | 589 |

<210> SEQ ID NO 18
<211> LENGTH: 816
<212> TYPE: DNA
<213> ORGANISM: Streptomyces kanamyceticus

<400> SEQUENCE: 18

| | | | | | |
|---|---|---|---|---|---|
| atgagccata | ttcaacggga | aacgtcttgc | tctaggccgc | gattaaattc | caacatggat | 60 |
| gctgatttat | atgggtataa | atgggctcgc | gataatgtcg | ggcaatcagg | tgcgacaatc | 120 |
| tatcgattgt | atgggaagcc | cgatgcgcca | gagttgtttc | tgaaacatgg | caaaggtagc | 180 |
| gttgccaatg | atgttacaga | tgagatggtc | agactaaact | ggctgacgga | atttatgcct | 240 |
| cttccgacca | tcaagcattt | tatccgtact | cctgatgatg | catggttact | caccactgcg | 300 |
| atccctggga | aaacagcatt | ccaggtatta | gaagaatatc | ctgattcagg | tgaaaatatt | 360 |
| gttgatgcgc | tggcagtgtt | cctgcgccgg | ttgcattcga | ttcctgtttg | taattgtcct | 420 |
| tttaacagcg | atcgcgtatt | tcgtctcgct | caggcgcaat | cacgaatgaa | taacggtttg | 480 |
| gttgatgcga | gtgattttga | tgacgagcgt | aatggctggc | ctgttgaaca | agtctggaaa | 540 |
| gaaatgcata | aacttttgcc | attctcaccg | gattcagtcg | tcactcatgg | tgatttctca | 600 |
| cttgataacc | ttatttttga | cgaggggaaa | ttaataggtt | gtattgatgt | tggacgagtc | 660 |
| ggaatcgcag | accgatacca | ggatcttgcc | atcctatgga | actgcctcgg | tgagttttct | 720 |
| ccttcattac | agaaacggct | ttttcaaaaa | tatggtattg | ataatcctga | tatgaataaa | 780 |
| ttgcagtttc | atttgatgct | cgatgagttt | ttctaa | | | 816 |

<210> SEQ ID NO 19
<211> LENGTH: 105
<212> TYPE: DNA
<213> ORGANISM: Pseudomonas aeruginosa

<400> SEQUENCE: 19

| | | | | | |
|---|---|---|---|---|---|
| cgcggaaccc | ctatttgttt | atttttctaa | atacattcaa | atatgtatcc | gctcatgaga | 60 |
| caataaccct | gataaatgct | tcaataatat | tgaaaaagga | agagt | | 105 |

<210> SEQ ID NO 20
<211> LENGTH: 796
<212> TYPE: DNA

```
<213> ORGANISM: Artificial Sequence
<220> FEATURE:
<223> OTHER INFORMATION: cBh promoter

<400> SEQUENCE: 20
tacataactt acggtaaatg gcccgcctgg ctgaccgccc aacgacccc gcccattgac      60 gtcaatagta acgccaatag ggactttcca ttgacgtcaa tgggtggagt atttacggta    120
aactgcccac ttggcagtac atcaagtgta tcatatgcca agtacgcccc ctattgacgt    180
caatgacggt aaatggcccg cctggcattg tgcccagtac atgaccttat gggactttcc    240
tacttggcag tacatctacg tattagtcat cgctattacc atggtcgagg tgagccccac    300
gttctgcttc actctcccca tctcccccc ctccccaccc ccaattttgt atttatttat     360
tttttaatta ttttgtgcag cgatggggc ggggggggg gggggcgcg cgccaggcgg       420 ggcggggcgg ggcgagggc ggggcgggc gaggcggaga ggtgcggcgg cagccaatca      480
gagcggcgcg ctccgaaagt ttccttttat ggcgaggcgg cggcggcggc ggccctataa    540
aaagcgaagc gcgcggcggg cgggagtcgc tgcgcgctgc cttcgcccg tgccccgctc     600 cgccgccgcc tcgcgccgcc cgccccggct ctgactgacc gcgttactcc cacaggtgag    660
cgggcgggac ggcccttctc ctccgggctg taattagctg agcaagaggt aagggtttaa    720
gggatggttg gttggtgggg tattaatgtt taattacctg gagcacctgc ctgaaatcac    780
tttttttcag gttgga                                                    796

<210> SEQ ID NO 21
<211> LENGTH: 254
<212> TYPE: DNA
<213> ORGANISM: Bos taurus

<400> SEQUENCE: 21
ctcgactgtg ccttctagtt gccagccatc tgttgtttgc ccctccccg tgccttcctt      60 gaccctggaa ggtgccactc ccactgtcct ttcctaataa aatgaggaaa ttgcatcgca    120
ttgtctgagt aggtgtcatt ctattctggg gggtggggtg gggcaggaca gcaagggga    180 ggattgggaa gacaacagca ggcatgctgg ggatgcggtg ggctctatgg cttctgaggc    240
ggaaagaacc agct                                                     254
```

RECOMBINANT ADENO-ASSOCIATED VIRAL VECTOR FOR GENE DELIVERY

CROSS REFERENCE TO RELATED APPLICATIONS

This application claims priority to U.S. Provisional Application No. 62/932,828, filed Nov. 8, 2019, which is incorporated by reference herein in its entirety for all purposes.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Nov. 7, 2020, is named "426871-000170_ST25(005).txt" and is about 22.4 kilobytes in size.

BACKGROUND

The SURF1 gene encodes the Surfeit locus protein 1 (SURF1) protein. SURF1 deficiency is a recessively inherited mitochondrial disorder and is the most frequent cause of Leigh syndrome (LS) associated with cytochrome c oxidase (COX, complex IV) deficiency.

The protein encoded by SURF1 is a component of the mitochondrial translation regulation assembly intermediate of cytochrome c oxidase complex (MITRAC complex), which is involved in the regulation of cytochrome c oxidase assembly.

Defects in the SURF1 gene are a cause of Leigh syndrome and Charcot-Marie-Tooth disease 4k (CMT4K), severe neurological disorders that are commonly associated with cytochrome c oxidase (complex IV) deficiency and lactic acidosis.

Compositions and methods provided herein solve the problem of a lack of reagents to study the effects of gene replacement in SURF1 genetic disorders. Furthermore, the delivery of a SURF1 gene in SURF1 deficiency patients is therapeutic, which represents a transformative treatment to address unmet medical needs of these patients.

SUMMARY

The present disclosure relates generally to the field of gene therapy and in particular, to recombinant adeno-associated viral (AAV) vector particles (also known as rAAV viral vectors) comprising transgene nucleic acid molecules encoding for SURF1, their manufacture, and their use to deliver transgenes to treat or prevent a disease or disorder, including SURF1 deficiency, Leigh Syndrome, mitochondrial complex IV deficiency and Charcot-Marie-Tooth disease 4K.

The present disclosure provides a recombinant adeno-associated virus (rAAV) vector comprising in 5' to 3' direction, (a) a first AAV inverted terminal repeat (ITR) sequence; (b) a promoter sequence; (c) a transgene nucleic acid molecule, wherein the transgene nucleic acid molecule comprises a nucleic acid sequence encoding for a SURF1 polypeptide, (d) a polyA sequence; and (e) a second AAV ITR sequence.

A SURF1 polypeptide comprises an amino acid sequence set forth in SEQ ID NO: 2.

In some aspects, the transgene nucleic acid molecule is a codon optimized transgene nucleic acid molecule.

In some aspects, the codon optimized transgene nucleic acid molecule comprises a nucleic acid sequence set forth in SEQ ID NO: 9. In some aspects, the codon optimized transgene nucleic acid molecule comprises a nucleic acid sequence set forth in SEQ ID NO: 3. In some aspects, the codon optimized transgene nucleic acid molecule comprises a nucleic acid sequence set forth in SEQ ID NO: 6.

In some aspects, the codon optimized sequence encoding a SURF1 polypeptide exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence.

In some aspects, the first AAV ITR sequence comprises a nucleic acid sequence set forth in SEQ ID NO: 12. In some aspects, wherein the second AAV ITR sequence comprises a nucleic acid sequence set forth in SEQ ID NO: 13.

In some aspects, the promoter comprises a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1a promoter, a U1b promoter, an MeCP2 promoter, an MeP418 promoter, an MeP426 promoter, a minimal MeCP2 promoter, a VMD2 promoter, an mRho promoter, EF1a promoter, Ubc promoter, human β-actin promoter, TRE promoter, Ac5 promoter, Polyhedrin promoter, CaMKIIa promoter, Gal1 promoter, TEF1 promoter, GDS promoter, ADH1 promoter, Ubi promoter, or α-1-antitrypsin (hAAT) promoter. In some aspects, the promoter sequence comprises a nucleic acid sequence set forth in SEQ ID NO: 20. In some aspects, the promoter sequence comprises a nucleic acid sequence set forth in SEQ ID NO: 14.

In some aspects, the polyA sequence comprises a nucleic acid sequence set forth in SEQ ID NO: 21.

The present disclosure provides a rAAV vector comprising, in the 5' to 3' direction a) a first AAV ITR sequence comprising the nucleic acid sequence set forth in SEQ ID NO: 12; b) a promoter sequence comprising the nucleic acid sequence set forth in SEQ ID NO: 20; c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence set forth in SEQ ID NO: 10; d) a polyA sequence comprising the nucleic acid sequence set forth in SEQ ID NO: 21; and e) a second AAV ITR sequence comprising the nucleic acid sequence set forth in SEQ ID NO: 13.

The present disclosure provides a rAAV vector comprising, comprising, in the 5' to 3' direction a) a first AAV ITR sequence comprising the nucleic acid sequence set forth in SEQ ID NO: 12; b) a promoter sequence comprising the nucleic acid sequence set forth in SEQ ID NO: 20; c) a transgene nucleic acid molecule, wherein the transgene nucleic acid molecule comprises a nucleic acid sequence encoding for a SURF1 polypeptide, wherein the nucleic acid sequence encoding for a S polypeptide comprises the nucleic acid sequence set forth in SEQ ID NO: 10; d) a polyA sequence comprising the nucleic acid sequence set forth in SEQ ID NO: 21; and e) a second AAV ITR sequence comprising the nucleic acid sequence set forth in SEQ ID NO: 13.

The present disclosure provides an rAAV viral vector comprising (i) an AAV capsid protein; and (ii) an rAAV vector of any one of the preceding claims.

In some aspects, the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein. In some aspects, the AAV capsid protein is an AAV9 capsid protein.

The present disclosure provides a pharmaceutical composition comprising: a) the rAAV viral vector of the disclosure; and at least one pharmaceutically acceptable excipient and/or additive.

The present disclosure provides a method for treating a subject having a disease and/or disorder involving a SURF1 gene, the method comprising administering to the subject at least one therapeutically effective amount of the rAAV viral vector of the disclosure or the pharmaceutical composition of the disclosure.

In some aspects, the disease and/or disorder involving a SURF1 gene is SURF1 deficiency, Leigh Syndrome, Mitochondrial complex IV deficiency or Charcot-Marie-Tooth disease 4K.

In some aspects, the rAAV viral vector or the pharmaceutical composition is administered to the subject at a dose ranging from about $10^{12}$ vector particles to about $10^{16}$ vector particles.

In some aspects, the rAAV viral vector or the pharmaceutical composition is administered to the subject at a dose of about $10^{14}$ vector particles to about $10^{15}$ vector particles.

In some aspects, the rAAV viral vector or the pharmaceutical composition is administered to the subject orally, rectally, transmucosally, inhalationally, transdermally, parenterally, intravenously, subcutaneously, intradermally, intramuscularly, intrapleurally, intracerebrally, intrathecally, intracerebrally, intraventricularly, intranasally, intra-aurally, intra-ocularly, or peri-ocularly, topically, intralymphatically, intracisternally, intranervally or intravitreally.

In some aspects, the rAAV viral vector or pharmaceutical composition is administered intrathecally.

In some aspects, the rAAV viral vector of the disclosure or the pharmaceutical composition of the disclosure for use in treating a disease and/or disorder involving a SURF1 gene in a subject in need thereof.

In some aspects, the disease and/or disorder involving a SURF1 gene is SURF1 deficiency, Leigh Syndrome, Mitochondrial complex IV deficiency or Charcot-Marie-Tooth disease 4K.

In some aspects, the rAAV viral vector or the pharmaceutical composition is for administration to the subject at a dose ranging from about $1\times10^{12}$ vector particles to about $1\times10^{16}$ vector particles.

In some aspects, the rAAV viral vector or the pharmaceutical composition is for administration to the subject at a dose of about $1\times10^{14}$ vector particles to about $1\times10^{15}$ vector particles.

In some aspects, the rAAV viral vector or the pharmaceutical composition is for administration to the subject orally, rectally, transmucosally, inhalationally, transdermally, parenterally, intravenously, subcutaneously, intradermally, intramuscularly, intrapleurally, intracerebrally, intrathecally, intracerebrally, intraventricularly, intranasally, intra-aurally, intra-ocularly, or peri-ocularly, topically, intralymphatically, intracisternally, intranervally, or intravitreally.

In some aspects, the rAAV viral vector or pharmaceutical composition is for administration intrathecally.

Any of the above aspects, or any other aspect described herein, can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more elements. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

FIG. 4A depicts COX activity of cerebrum (n=10-18 per group) of WT and SURF1 KO mice with assigned treatments.

4C depicts liver (n=5-8 per group) of WT and SURF1 KO mice with assigned treatments.

DETAILED DESCRIPTION

Figure 1:
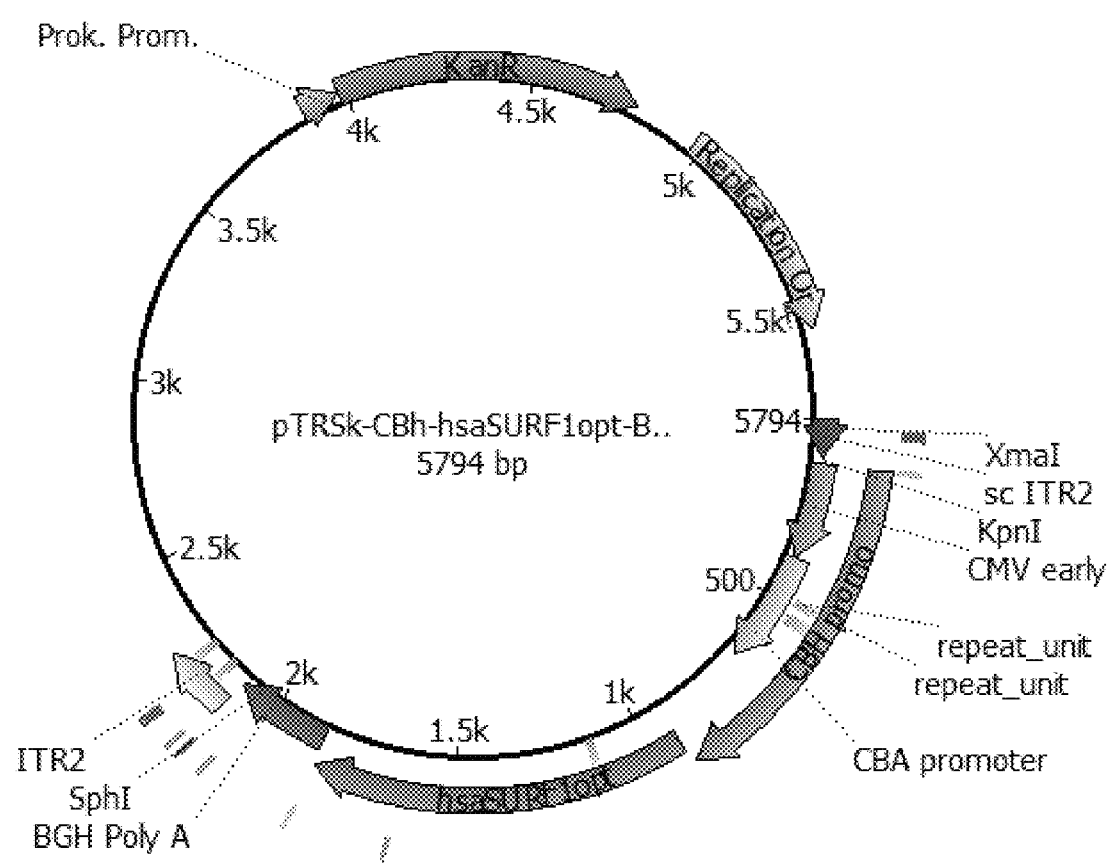
FIG. 1 is a bacterial plasmid map depicting a codon optimized SURF1 recombinant adeno-associated virus (rAAV) vector.

The present disclosure provides, inter alia, isolated polynucleotides, recombinant adeno-associated virus (rAAV) vectors, and rAAV viral vectors comprising transgene nucleic acid molecules encoding for SURF1. The present disclosure also provides methods of manufacturing these isolated polynucleotides, rAAV vectors, and rAAV viral vectors, as well as their use to deliver transgenes to treat or prevent a disease or disorder, including diseases associated with loss and/or misfunction of a SURF1 gene. In some aspects, diseases associated with loss and/or misfunction of a SURF1 gene include Leigh Syndrome, Mitochondrial complex IV deficiency and Charcot-Marie-Tooth disease 4K.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types. At least 11 sequentially numbered AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAVPHP.B. The AAV particle comprises, consists essentially of, or consists of three major viral proteins: VP1, VP2 and VP3. In some aspects, the AAV refers to the serotype AAV1, AAV2, AAV4, AAV5, AAV6, AAV7, AAV8, AAV9, AAV10, AAV11, AAV12, AAV13, AAVPHP.B, AAVrh74, or AAVrh.10.

Exemplary adeno-associated viruses and recombinant adeno-associated viruses include, but are not limited to all serotypes (e.g., AAV1, AAV2, AAV3, AAV4, AAV5, AAV6, AAV7, AAV8, AAV9, AAV10, AAV11, AAV12, AAV13, AAVPHP.B, AAVrh74, and AAVrh.10). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03, AAV-KP-1 (described in detail in Kerun et al. JCI Insight, 2019; 4(22):e131610) and AAV-NP59 (described in detail in Paulk et al. Molecular Therapy, 2018; 26(1): 289-303).

AAV Structure and Function

AAV is a replication-deficient parvovirus, the single-stranded DNA genome of which is about 4.7 kb in length, including two 145-nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference in its entirety. U.S. Pat. No. 9,434,928 also provides the sequences of the capsid proteins and a self-complementary genome. In one aspect, an AVV genome is a self-complementary genome. Cis-acting sequences directing viral DNA replication (rep), encapsidation/packaging, and host cell chromosome integration are contained within AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome.

The cap gene is expressed from the p40 promoter and encodes the three capsid proteins, VP1, VP2, and VP3. Alternative splicing and non-consensus translational start sites are responsible for the production of the three related capsid proteins. More specifically, after the single mRNA from which each of the VP1, VP2 and VP3 proteins are translated is transcribed, it can be spliced in two different manners: either a longer or shorter intron can be excised, resulting in the formation of two pools of mRNAs: a 2.3 kb- and a 2.6 kb-long mRNA pool. The longer intron is often preferred and thus the 2.3-kb-long mRNA can be called the major splice variant. This form lacks the first AUG codon, from which the synthesis of VP1 protein starts, resulting in a reduced overall level of VP1 protein synthesis. The first AUG codon that remains in the major splice variant is the initiation codon for the VP3 protein. However, upstream of that codon in the same open reading frame lies an ACG sequence (encoding threonine) which is surrounded by an optimal Kozak (translation initiation) context. This contributes to a low level of synthesis of the VP2 protein, which is actually the VP3 protein with additional N terminal residues, as is VP1, as described in Becerra S P et al., (December 1985). "Direct mapping of adeno-associated virus capsid proteins B and C: a possible ACG initiation codon". Proceedings of the National Academy of Sciences of the United States of America. 82 (23): 7919-23, Cassinotti P et al., (November 1988). "Organization of the adeno-associated virus (AAV) capsid gene: mapping of a minor spliced mRNA coding for virus capsid protein 1". Virology. 167 (1): 176-84, Muralidhar S et al., (January 1994). "Site-directed mutagenesis of adeno-associated virus type 2 structural protein initiation codons: effects on regulation of synthesis and biological activity". Journal of Virology. 68 (1): 170-6, and Trempe J P, Carter B J (September 1988). "Alternate mRNA splicing is required for synthesis of adeno-associated virus VP1 capsid protein". Journal of Virology. 62 (9): 3356-63, each of which is herein incorporated by reference. A single consensus polyA site is located at map position 95 of the AAV genome. The life cycle and genetics of AAV are reviewed in Muzyczka, Current Topics in Microbiology and Immunology, 158: 97-129 (1992).

Each VP1 protein contains a VP1 portion, a VP2 portion and a VP3 portion. The VP1 portion is the N-terminal portion of the VP1 protein that is unique to the VP1 protein. The VP2 portion is the amino acid sequence present within the VP1 protein that is also found in the N-terminal portion of the VP2 protein. The VP3 portion and the VP3 protein have the same sequence. The VP3 portion is the C-terminal portion of the VP1 protein that is shared with the VP1 and VP2 proteins.

The VP3 protein can be further divided into discrete variable surface regions I-IX (VR-I-IX). Each of the variable surface regions (VRs) can comprise or contain specific amino acid sequences that either alone or in combination with the specific amino acid sequences of each of the other VRs can confer unique infection phenotypes (e.g., decreased antigenicity, improved transduction and/or tissue-specific tropism relative to other AAV serotypes) to a particular serotype as described in DiMatta et al., "Structural Insight into the Unique Properties of Adeno-Associated Virus Serotype 9" J. Virol., Vol. 86 (12): 6947-6958, June 2012, the contents of which are incorporated herein by reference.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple studies have demonstrated long-term (>1.5 years) recombinant AAV-mediated protein expression in muscle. See, Clark et al., Hum Gene Ther, 8: 659-669 (1997); Kessler et al., Proc Nat. Acad Sc. USA, 93: 14082-14087 (1996); and Xiao et al., J Virol, 70: 8098-8108 (1996). See also, Chao et al., Mol Ther, 2:619-623 (2000) and Chao et al., Mol Ther, 4:217-222 (2001). Moreover, because muscle is highly vascularized, recombinant AAV transduction has resulted in the appearance of transgene products in the systemic circulation following intramuscular injection as described in Herzog et al., Proc Natl Acad Sci USA, 94: 5804-5809 (1997) and Murphy et al., Proc Natl Acad Sci USA, 94: 13921-13926 (1997). Moreover, Lewis et al., J Virol, 76: 8769-8775 (2002) demonstrated that skeletal myofibers possess the necessary cellular factors for correct antibody glycosylation, folding, and secretion, indicating that muscle is capable of stable expression of secreted protein therapeutics. Recombinant AAV (rAAV) genomes of the invention comprise, consist essentially of, or consist of a nucleic acid molecule encoding a therapeutic protein (e.g., SURF1) and one or more AAV ITRs flanking the nucleic acid molecule. AAV DNA in the rAAV genomes may be from any AAV serotype for which a recombinant virus can be derived including, but not limited to, AAV serotypes AAV1, AAV2, AAV3, AAV4, AAV5, AAV6, AAV7, AAV8, AAV9, AAV10, AAV11, AAV12, AAV13, AAVPHP.B, AAVrh74, and AAVrh.10. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

Isolated Polynucleotides Comprising Transgene Nucleic Acid Molecules

The present disclosure provides isolated polynucleotides comprising at least one transgene nucleic acid molecule.

In some aspects, a transgene nucleic acid molecule can comprise a nucleic acid sequence encoding a SURF1 polypeptide, or at least one fragment thereof. As would be appreciated by the skilled artisan, SURF1 is encoded for by the SURF1 gene in the human genome. Thus, a transgene nucleic acid molecule can comprise, consist essentially of, or consist of an SURF1 sequence, or any fragment thereof. In some aspects, a transgene nucleic acid molecule can comprise a nucleic acid sequence encoding a biological equivalent of a SURF1 polypeptide.

In some aspects, a SURF1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 1 or SEQ ID NO: 2.

In some aspects, a SURF1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence put forth in SEQ ID NO: 1 or SEQ ID NO: 2.

In some aspects, a nucleic acid sequence encoding a SURF1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to any one of the nucleic acid sequences put forth in SEQ ID NOs: 3-10. In some aspects, a nucleic acid sequence encoding a SURF1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NOs: 10. A nucleic acid sequence encoding a SURF1 polypeptide can be referred to as a SURF1 sequence.

In some aspects, the nucleic acid sequence encoding a SURF1 polypeptide can be a codon optimized nucleic acid sequence that encodes for a SURF1 polypeptide. A codon optimized nucleic acid sequence encoding a SURF1 polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the SURF1 polypeptide. As used herein, the "wildtype human nucleic acid sequence of the SURF1 polypeptide" refers to the nucleic acid sequence that encodes the SURF1 polypeptide in a human genome, as put forth in SEQ ID NO: 11.

SEQ ID NOs: 3-10 are unique codon optimized nucleic acid sequences that encode for a SURF1 polypeptide.

In some aspects, a codon optimized nucleic acid sequence encoding a SURF1 polypeptide such as those put forth in SEQ ID NOs: 3-10, can comprise no donor splice sites. In some aspects, a codon optimized nucleic acid sequence encoding a SURF1 polypeptide can comprise no more than about one, or about two, or about three, or about four, or about five, or about six, or about seven, or about eight, or about nine, or about ten donor splice sites. In some aspects, a codon optimized nucleic acid sequence encoding a SURF1 polypeptide comprises at least one, or at least two, or at least three, or at least four, or at least five, or at least six, or at least seven, or at least eight, or at least nine, or at least ten fewer donor splice sites as compared to the wildtype human nucleic acid sequence the SURF1 polypeptide. Without wishing to be bound by theory, the removal of donor splice sites in the codon optimized nucleic acid sequence can unexpectedly and unpredictably increase expression of the SURF1 polypeptide in vivo, as cryptic splicing is prevented. Moreover, cryptic splicing may vary between different subjects, meaning that the expression level of the SURF1 polypeptide comprising donor splice sites may unpredictably vary between different subjects. Such unpredictability is unacceptable in the context of human therapy. Accordingly, the codon optimized nucleic acid sequences put forth in SEQ ID NOs: 3-10, which lacks donor splice sites, unexpectedly and surprisingly allows for increased expression of the SURF1 polypeptide in human subjects and regularizes expression of the SURF1 polypeptide across different human subjects.

In some aspects, a codon optimized nucleic acid sequence encoding a SURF1 polypeptide, such as those put forth in SEQ ID NOs: 3-10, can have a GC content that differs from the GC content of the wildtype human nucleic acid sequence the SURF1 polypeptide. In some aspects, the GC content of a codon optimized nucleic acid sequence encoding a SURF1 polypeptide is more evenly distributed across the entire nucleic acid sequence, as compared to the wildtype human nucleic acid sequence the SURF1 polypeptide. Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, a codon optimized nucleic acid sequence encoding a SURF1 polypeptide, such as those put forth in SEQ ID NOs: 3-10, can have fewer repressive microRNA target binding sites as compared to the wildtype human nucleic acid sequence the SURF1 polypeptide. In some aspects, a codon optimized nucleic acid sequence encoding a SURF1 polypeptide can have at least one, or at least two, or at least three, or at least four, or at least five, or at least six, or at least seven, or at least eight, or at least nine, or at least ten, or at least ten fewer repressive microRNA target binding sites as compared to the wildtype human nucleic acid sequence the SURF1 polypeptide. Without wishing to be bound by theory, by having fewer repressive microRNA target binding sites, the codon optimized nucleic acid sequence encoding a SURF1 polypeptide unexpectedly exhibits increased expression in a human subject.

In some aspects, the codon optimized nucleic acid sequence encoding a SURF1 polypeptide exhibits at least 5%, at least 10%, at least 20%, at least 30%, at least 50%, at least 75%, at least 100%, at least 200%, at least 300%, at least 500%, or at least 1000% increased expression in a human subject relative to a wild-type or non-codon optimized nucleic acid sequence encoding a SURF1 polypeptide.

AAV Vectors

In some aspects, the isolated polynucleotides comprising at least one transgene nucleic acid sequence described herein can be a recombinant AAV (rAAV) vector.

As used herein, the term "vector" refers to a nucleic acid comprising, consisting essentially of, or consisting of an intact replicon such that the vector may be replicated when placed within a cell, for example by a process of transfection, infection, or transformation. It is understood in the art that once inside a cell, a vector may replicate as an extrachromosomal (episomal) element or may be integrated into a host cell chromosome. Vectors may include nucleic acids derived from retroviruses, adenoviruses, herpesvirus, baculoviruses, modified baculoviruses, papovaviruses, or otherwise modified naturally-occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, consisting essentially of, or consisting of DNA condensed with cationic polymers such as heterogeneous polylysine, defined-length oligopeptides, and polyethyleneimine, in some cases contained in liposomes; and the use of ternary complexes comprising, consisting essentially of, or consisting of a virus and polylysine-DNA.

With respect to general recombinant techniques, vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif) and Promega Biotech (Madison, Wis.). In order to optimize expression and/or in vitro transcription, it may be necessary to remove, add or alter 5' and/or 3' untranslated portions of cloned transgenes to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

An "rAAV vector" as used herein refers to a vector comprising, consisting essentially of, or consisting of one or more transgene nucleic acid molecules and one or more AAV inverted terminal repeat sequences (ITRs). Such AAV vectors can be replicated and packaged into infectious viral particles when present in a host cell that provides the functionality of rep and cap gene products; for example, by transfection of the host cell. In some aspects, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing rAAV vectors may also contain elements for manufacturing purposes, e.g., antibiotic resistance genes, origin of replication sequences etc., but these are not encapsidated and thus do not form part of the AAV particle.

In some aspects, an rAAV vector can comprise at least one transgene nucleic acid molecule. In some aspects, an rAAV vector can comprise at least one AAV inverted terminal (ITR) sequence. In some aspects, an rAAV vector can comprise at least one promoter sequence. In some aspects, an rAAV vector can comprise at least one enhancer sequence. In some aspects, an rAAV vector can comprise at least one polyA sequence. In some aspects, an rAAV vector can comprise at least one origin of replication sequence. In some aspects, an rAAV vector can comprise at least one self-cleaving peptide sequence. In some aspects, an rAAV vector can comprise at least one antibiotic resistance gene. In some aspects, an rAAV vector can comprise at least one reporter protein.

In some aspects, an rAAV vector can comprise a first AAV ITR sequence, a promoter sequence, a transgene nucleic acid molecule, a polyA sequence, and a second AAV ITR sequence. In some aspects, an rAAV vector can comprise, in the 5' to 3' direction, a first AAV ITR sequence, a promoter sequence, a transgene nucleic acid molecule, a polyA sequence, and a second AAV ITR sequence.

In some aspects, an rAAV vector can comprise more than one transgene nucleic acid molecule. In some aspects, an rAAV vector can comprise at least two transgene nucleic acid molecule, such that the rAAV vector comprises a first transgene nucleic acid molecule and an at least second transgene nucleic acid molecule. In some aspects, the first and the at least second transgene nucleic acid molecules can comprise the same sequence. In some aspects, the first and the at least second transgene nucleic acid molecules can comprise different sequence. In some aspects, the first and the at least second transgene nucleic acid molecules can be adjacent to each other. In some aspects, the first and the at least second transgene nucleic acid molecules can be separated by at least one self-cleaving peptide sequence.

In some aspects, an rAAV vector can comprise more than one promoter sequence. In some aspects, an rAAV vector can comprise at least two promoter sequences, such that the rAAV vector comprises a first promoter sequence and an at least second promoter sequence. In some aspects, the first and the at least second promoter sequences can comprise the same sequence. In some aspects, the first and the at least second promoter sequences can comprise different sequences. In some aspects, the first and the at least second promoter sequences can be adjacent to each other. In some aspects wherein an rAAV vector also comprises a first transgene nucleic acid molecule and an at least second transgene nucleic acid molecule, the first promoter can be located upstream (5') of the first transgene nucleic acid molecule and the at least second promoter can be located between the first transgene nucleic acid molecule and the at least second transgene nucleic acid molecule, such that the at least second promoter is downstream (3') of the first transgene nucleic acid molecule and upstream (5') of the at least second transgene nucleic acid molecule.

Any of the preceding rAAV vectors can further comprise at least one enhancer. The at least one enhancer can be located anywhere in the rAAV vector. In some aspects, the at least one enhancer can be located immediately upstream (5') of a promoter. Thus, an rAAV vector can comprise, in the 5' to 3' direction, a first AAV ITR sequence, an enhancer, a promoter sequence, a transgene nucleic acid molecule, a polyA sequence, and a second AAV ITR sequence. In some aspects, the at least one enhancer can be located immediately downstream (3') of a promoter. Thus, an rAAV vector can comprise, in the 5' to 3' direction, a first AAV ITR sequence, a promoter sequence, an enhancer, a transgene nucleic acid molecule, a polyA sequence, and a second AAV ITR sequence. In some aspects, the at least one enhancer can be located immediately downstream of a transgene nucleic acid molecule. Thus, an rAAV vector can comprise, in the 5' to 3' direction, a first AAV ITR sequence, a promoter sequence, a transgene nucleic acid molecule, an enhancer, a polyA sequence, and a second AAV ITR sequence.

AAV ITR Sequences

In some aspects, an AAV ITR sequence can comprise any AAV ITR sequence known in the art. In some aspects, an AAV ITR sequence can be an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh.10 ITR sequence.

Thus, in some aspects, an AAV ITR sequence can comprise, consist essentially of, or consist of an AAV1 ITR sequence, an AAV2 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAV11 ITR sequence, an AAV12 ITR sequence, an AAV13 ITR sequence, an AAVrh74 ITR sequence, or an AAVrh.10 ITR sequence.

In some aspects, an rAAV vector of the present disclosure can comprise, consist essentially of, or consist of AAV2 ITR sequences. In some aspects, an rAAV vector of the present disclosure can comprise, consist essentially of, or consist of AAV2 ITR sequences or a modified AAV2 ITR sequence.

In some aspects, an AAV2 ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12.

In some aspects, a modified AAV2 ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13.

In some aspects, a first AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 13 and a second AAV ITR sequence can comprise consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 12.

Promoter Sequence and Enhancers

The term "promoter" and "promoter sequence" as used herein means a control sequence that is a region of a polynucleotide sequence at which the initiation and rate of transcription of a coding sequence, such as a gene or a transgene, are controlled. Promoters may be constitutive, inducible, repressible, or tissue-specific, for example. Promoters may contain genetic elements at which regulatory proteins and molecules such as RNA polymerase and transcription factors may bind. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, an H1 promoter, a ubiquitous chicken β-actin hybrid (CBh) promoter, a small nuclear RNA (U1a or U1b) promoter, an MeCP2 promoter, an MeP418 promoter, an MeP426 promoter, a minimal MeCP2 promoter, a VMD2 promoter, an mRho promoter or an EF1 promoter.

Additional non-limiting exemplary promoters provided herein include, but are not limited to EF1a, Ubc, human β-actin, CAG, TRE, Ac5, Polyhedrin, CaMKIIa, Gal1, TEF1, GDS, ADH1, Ubi, and α-1-antitrypsin (hAAT). It is known in the art that the nucleotide sequences of such promoters may be modified in order to increase or decrease the efficiency of mRNA transcription. See, e.g., Gao et al. (2018) Mol. Ther.: Nucleic Acids 12:135-145 (modifying TATA box of 7SK, U6 and H1 promoters to abolish RNA polymerase III transcription and stimulate RNA polymerase II-dependent mRNA transcription). Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters. In some aspects, the promoter is used together with at least one enhancer to increase the transcription efficiency. Non-limiting examples of enhancers include an interstitial retinoid-binding protein (IRBP) enhancer, an RSV enhancer or a CMV enhancer.

In some aspects, a promoter sequence can comprise, consist essentially of, or consist of a Rous sarcoma virus (RSV) LTR promoter sequence (optionally with the RSV enhancer), a cytomegalovirus (CMV) promoter sequence, an SV40 promoter sequence, a dihydrofolate reductase promoter sequence, a β-actin promoter sequence, a phosphoglycerol kinase (PGK) promoter sequence, a U6 promoter sequence, an H1 promoter sequence, a ubiquitous chicken β-actin hybrid (CBh) promoter sequence, a small nuclear RNA (U1a or U1b) promoter sequence, an MeCP2 promoter sequence, an MeP418 promoter sequence, an MeP426 promoter sequence, a minimal MeCP2 promoter sequence, a VMD2 promoter sequence, an mRho promoter sequence, an EFI promoter sequence, an EF1a promoter sequence, a Ubc promoter sequence, a human β-actin promoter sequence, a CAG promoter sequence, a TRE promoter sequence, an Ac5 promoter sequence, a Polyhedrin promoter sequence, a CaMKIIa promoter sequence, a Gal1 promoter sequence, a TEF1 promoter sequence, a GDS promoter sequence, an ADH1 promoter sequence, a Ubi promoter sequence or an α-1-antitrypsin (hAAT) promoter sequence.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter. Non-limiting examples of linked enhancer/promoter for use in the methods, compositions and constructs provided herein include a PDE promoter plus IRBP enhancer or a CMV enhancer plus U1a promoter. It is understood in the art that enhancers can operate from a distance and irrespective of their orientation relative to the location of an endogenous or heterologous promoter. It is thus further understood that an enhancer operating at a distance from a promoter is thus "operably linked" to that promoter irrespective of its location in the vector or its orientation relative to the location of the promoter.

As used throughout the disclosure, the term "operably linked" refers to the expression of a gene (i.e. a transgene) that is under the control of a promoter with which it is spatially connected. A promoter can be positioned 5' (upstream) or 3' (downstream) of a gene under its control. A promoter can be positioned 5'(upstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

In some aspects, a promoter sequence can comprise, consist essentially of, or consist of a JeT promoter sequence. A JeT promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 14.

In some aspects, a promoter sequence can comprise, consist essentially of, or consist of a MeP229 promoter sequence. A meP229 promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 15.

In some aspects, a promoter sequence can comprise, consist essentially of, or consist of a CBh promoter sequence. A CBh promoter sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 20.

In some aspects, bacterial plasmids of the present disclosure can comprise a prokaryotic promoter.

A prokaryotic promoter can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 19.
Transgene Nucleic Acid Molecules In some aspects, a transgene nucleic acid molecules can comprise a nucleic acid molecule encoding a SURF1 polypeptide, or at least one fragment thereof. In some aspects, a transgene nucleic acid molecule can comprise a nucleic acid sequence encoding a biological equivalent of a SURF1 polypeptide, or at least one fragment thereof.

In some aspects, a SURF1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to the amino acid sequence put forth in SEQ ID NO: 1 or SEQ ID NO: 2, or a fragment thereof. In some aspects, a SURF1 polypeptide comprises, consists essentially of, or consists of an amino acid sequence at least 65%, 70%, 75%, 80%, 85%, 90%, 95%, 96%, 97%, 98%, 99% or 100% (or any percentage in between) identical to at least one portion of the amino acid sequence put forth in SEQ ID NO: 1, or a fragment thereof.

In some aspects, a nucleic acid sequence encoding a SURF1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to any one of the nucleic acid sequences put forth in SEQ ID NOs: 3-10. In some aspects, a nucleic acid sequence encoding a SURF1 polypeptide comprises, consists essentially of, or consists of a nucleic acid sequence at least 65%, 70%, 75%, 80%, 85%, 90%, 95%, 96%, 97%, 98%, 99% or 100% (or any percentage in between) identical to the nucleic acid sequences put forth in SEQ ID NOs: 6. A nucleic acid sequence encoding a SURF1 polypeptide can be referred to as a SURF1 nucleic acid molecule.

In some aspects, a nucleic acid sequence encoding a SURF1 polypeptide can be a codon optimized nucleic acid sequence that encodes for a SURF1 polypeptide. A codon optimized nucleic acid sequence encoding a SURF1 polypeptide can comprise, consist essentially of, or consist of a nucleic acid sequence that is no more than 65%, 70%, 75%, 80%, 85%, 90%, 95%, 96%, 97%, 98%, 99% (or any percentage in between) identical to the wildtype human nucleic acid sequence encoding the SURF1 polypeptide. As used herein, the "wildtype human nucleic acid sequence encoding the SURF1 polypeptide" refers to the nucleic acid sequence that encodes the SURF1 polypeptide in a human genome, as put forth in, for example, SEQ ID NO: 11.

SEQ ID NOs: 3-10 are unique codon optimized nucleic acid sequences that encode for a SURF1 polypeptide.

In some aspects, a transgene nucleic acid molecule can comprise, consist essentially of, or consist of a nucleic acid sequence encoding a reporter protein. As used herein, a reporter protein is a detectable protein that is operably linked to a promoter to assay the expression (for example, tissue specificity and/or strength) of the promoter. In aspects, a reporter protein may be operably linked to a polypeptide. In aspects, reporter proteins may be used in monitoring DNA delivery methods, functional identification and characterization of promoter and enhancer elements, translation and transcription regulation, mRNA processing and protein: protein interactions. Non-limiting examples of a reporter protein are β-galactosidase; a fluorescent protein, such as, Green Fluorescent Protein (GFP) or Red Fluorescent Protein (RFP); luciferase; glutathione S-transferase; and maltose binding protein.

In some aspects, a transgene nucleic acid molecule can further comprise a nucleic acid sequence encoding a signal peptide.

In some aspects, the SURF1 polypeptide can comprise a signal peptide or signal polypeptide.

polyA Sequences

In some aspects, a polyadenylation (polyA) sequence can comprise any polyA sequence known in the art. Non-limiting examples of polyA sequences include, but are not limited to, an MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

Thus, a polyA sequence can comprise, consists essentially of or consist of an MeCP2 polyA sequence, a retinol dehydrogenase 1 (RDH1) polyA sequence, a bovine growth hormone (BGH) polyA sequence, an SV40 polyA sequence, a SPA49 polyA sequence, a sNRP-TK65 polyA sequence, a sNRP polyA sequence, or a TK65 polyA sequence.

In some aspects, a polyA sequence can comprise, consist essentially of, or consist of an SV40pA sequence. In some aspects, an SV40pA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NOs: 16.

In some aspects, a polyA sequence can comprise, consist essentially of, or consist of a BGHpA sequence. In some aspects, an BGHpA sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to any of the sequences put forth in SEQ ID NO: 21.

Bacterial Plasmids

In some aspects, the rAAV vectors of the present disclosure can be contained within a bacterial plasmid to allow for propagation of the rAAV vector in vitro. Thus, the present disclosure provides bacterial plasmids comprising any of the rAAV vectors described herein. A bacterial plasmid can further comprise an origin of replication sequence. A bacterial plasmid can further comprise an antibiotic resistance gene. A bacterial plasmid can further comprise a prokaryotic promoter.

Origin of Replication Sequence

In some aspects, an origin of replication sequence can comprise, consist essentially of, or consist of any origin of replication sequence known in the art (e.g., SEQ ID NO:17). The origin of replication sequence can be a bacterial origin of replication sequence, thereby allowing the rAAV vector comprising said bacterial origin of replication sequence to be produced, propagated and maintained in bacteria, using methods standard in the art.

Antibiotic Resistance Genes

In some aspects, rAAV vectors and rAAV viral vectors of the disclosure can comprise an antibiotic resistance gene.

In some aspects, an antibiotic resistance gene can comprise, consist essentially of, or consist of any antibiotic resistance genes known in the art. Examples of antibiotic resistance genes known in the art include, but are not limited to kanamycin resistance genes, spectinomycin resistance genes, streptomycin resistance genes, ampicillin resistance genes, carbenicillin resistance genes, bleomycin resistance genes, erythromycin resistance genes, polymyxin B resistance genes, tetracycline resistance genes and chloramphenicol resistance genes.

In some aspects, an antibiotic resistance gene can comprise, consist essentially of, or consist of a kanamycin antibiotic resistance gene. A kanamycin antibiotic resistance gene can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 18.

AAV Viral Vectors

A "viral vector" is defined as a recombinantly produced virus or viral particle that contains a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, e.g., Schlesinger and Dubensky (1999) Curr. Opin. Biotechnol. 5:434-439 and Ying, et al. (1999) Nat. Med. 5(7):823-827.

An "AAV virion" or "AAV viral particle" or "AAV viral vector" or "rAAV viral vector" or "AAV vector particle" or "AAV particle" refers to a viral particle composed of at least one AAV capsid protein and an encapsidated polynucleotide rAAV vector. Thus, production of an rAAV viral vector necessarily includes production of an rAAV vector, as such a vector is contained within an rAAV vector.

As used herein, the term "viral capsid" or "capsid" refers to the proteinaceous shell or coat of a viral particle. Capsids function to encapsidate, protect, transport, and release into the host cell a viral genome. Capsids are generally comprised of oligomeric structural subunits of protein ("capsid proteins"). As used herein, the term "encapsidated" means enclosed within a viral capsid. The viral capsid of AAV is composed of a mixture of three viral capsid proteins: VP1, VP2, and VP3. The mixture of VP1, VP2 and VP3 contains 60 monomers that are arranged in a T=1 icosahedral symmetry in a ratio of 1:1:10 (VP1:VP2:VP3) or 1:1:20 (VP1:VP2:VP3) as described in Sonntag F et al., (June 2010). "A viral assembly factor promotes AAV2 capsid formation in the nucleolus". Proceedings of the National Academy of Sciences of the United States of America. 107 (22): 10220-5, and Rabinowitz J E, Samulski R J (December 2000). "Building a better vector: the manipulation of AAV virions". Virology. 278 (2): 301-8, each of which is incorporated herein by reference in its entirety.

The present disclosure provides an rAAV viral vector comprising: a) any of the rAAV vectors described herein; and b) an AAV capsid protein.

An AAV capsid protein can be any AAV capsid protein known in the art. An AAV capsid protein can be an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

Alternative rAAV Vectors and rAAV Viral Vectors

The present disclosure provides the following embodiments:

1. An rAAV vector, comprising, in the 5' to 3' direction
a) a first AAV ITR sequence;
b) a promoter sequence;
c) a transgene nucleic acid molecule, wherein the transgene nucleic acid molecule comprises a nucleic acid sequence encoding for a SURF1 polypeptide;
d) a polyA sequence; and
e) a second AAV ITR sequence.

2. The rAAV vector of embodiment 1, wherein the nucleic acid sequence encoding for a SURF1 polypeptide is a codon optimized nucleic acid sequence.

3. The rAAV vector of embodiment 1 or embodiment 2, wherein the SURF1 polypeptide comprises the amino acid sequence of SEQ ID NO: 1 or SEQ ID NO: 2.

4. The rAAV vector of embodiment 3, wherein the SURF1 polypeptide comprises the amino acid sequence of SEQ ID NO: 1.

5. The rAAV vector of embodiment 3, wherein the SURF1 polypeptide comprises the amino acid sequence of SEQ ID NO: 2.

6. The rAAV vector of any one of the preceding embodiments, wherein the codon optimized transgene nucleic acid molecule eliminates a predicted donor splice site.

7. The rAAV vector of any one of the preceding embodiments, wherein the codon optimized transgene nucleic acid molecule has a higher GC content than the wild-type transgene nucleic acid molecule.

8. The rAAV vector of any one of the preceding embodiments, wherein the GC content of the codon optimized transgene nucleic acid molecule is more evenly distributed across the entire nucleic acid sequence as compared to the wild-type transgene nucleic acid molecule.

9. The rAAV vector of any one of the preceding embodiments, wherein the transgene nucleic acid molecule comprises any one of the nucleic acid sequences put forth in SEQ ID NOs: 3-10.

10. The rAAV vector of embodiment 9, wherein the transgene nucleic acid molecule comprises the nucleic acid sequence of SEQ ID NO: 3.

11. The rAAV vector of embodiment 9, wherein the transgene nucleic acid molecule comprises the nucleic acid sequence of SEQ ID NO: 4.

12. The rAAV vector of embodiment 9, wherein the transgene nucleic acid molecule comprises the nucleic acid sequence of SEQ ID NO: 5.

13. The rAAV vector of embodiment 9, wherein the transgene nucleic acid molecule comprises the nucleic acid sequence of SEQ ID NO: 6.

14. The rAAV vector of embodiment 9, wherein the transgene nucleic acid molecule comprises the nucleic acid sequence of SEQ ID NO: 7.

15. The rAAV vector of embodiment 9, wherein the transgene nucleic acid molecule comprises the nucleic acid sequence of SEQ ID NO: 8.

16. The rAAV vector of embodiment 9, wherein the transgene nucleic acid molecule comprises the nucleic acid sequence of SEQ ID NO: 9.

17. The rAAV vector of embodiment 9, wherein the transgene nucleic acid molecule comprises the nucleic acid sequence of SEQ ID NO: 10.

18. The rAAV vector of any one of the preceding embodiments, wherein the first AAV ITR sequence is an AAV2 ITR sequence.

19. The rAAV vector of any one of the preceding embodiments, wherein the first AAV ITR sequence comprises the nucleic acid sequence of SEQ ID NO: 12.

20. The rAAV vector of any one of the preceding embodiments, wherein the second AAV ITR sequence is a modified AAV2 ITR sequence.

21. The rAAV vector of any one of the preceding embodiments, wherein the second AAV ITR sequence comprises the nucleic acid sequence of SEQ ID NO: 13.

22. The rAAV vector of any one of the preceding embodiments, wherein the promoter sequence comprises a JeT promoter sequence.

23. The rAAV vector of embodiment 22, wherein the JeT promoter sequence comprises the nucleic acid sequence of SEQ ID NO: 14.

24. The rAAV vector of any one of the preceding embodiments, wherein the promoter sequence comprises a MeP229 promoter sequence.

25. The rAAV vector of embodiment 24, wherein the MeP229 promoter sequence comprises the nucleic acid sequence of SEQ ID NO: 15.

26. The rAAV vector of any one of the preceding embodiments, wherein the polyA sequence comprises an SV40pA sequence.

27. The rAAV vector of embodiment 26, wherein the SV40pA sequence comprises the nucleic acid sequence of SEQ ID NO: 16.

28. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 20;
   c) a transgene nucleic acid molecule, wherein the transgene nucleic acid molecule comprises a nucleic acid sequence encoding for a SURF1 polypeptide, wherein the SURF1 polypeptide comprises the amino acid sequence of SEQ ID NO: 1 or SEQ ID NO: 2;
   d) a polyA sequence comprising the nucleic acid sequence of SEQ ID NO: 21; and
   e) a second AAV ITR sequence comprising the nucleic acid sequence of SEQ ID NO: 13.

29. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 15;
   c) a transgene nucleic acid molecule, wherein the transgene nucleic acid molecule comprises a nucleic acid sequence encoding for a SURF1 polypeptide, wherein the SURF1 polypeptide comprises the amino acid sequence of SEQ ID NO: 1 or SEQ ID NO: 2;
   d) a polyA sequence comprising the nucleic acid sequence of SEQ ID NO: 21; and
   e) a second AAV ITR sequence comprising the nucleic acid sequence of SEQ ID NO: 13.

30. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 14;
   c) a transgene nucleic acid molecule, wherein the transgene nucleic acid molecule comprises a nucleic acid sequence encoding for a SURF1 polypeptide, wherein the SURF1 polypeptide comprises the amino acid sequence of SEQ ID NO: 1;
   d) a polyA sequence comprising the nucleic acid sequence of SEQ ID NO: 21; and
   e) a second AAV ITR sequence comprising the nucleic acid sequence of SEQ ID NO: 13.

31. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 15;
   c) a transgene nucleic acid molecule, wherein the transgene nucleic acid molecule comprises a nucleic acid sequence encoding for a SURF1 polypeptide, wherein the SURF1 polypeptide comprises the amino acid sequence of SEQ ID NO: 1;
   d) a polyA sequence comprising the nucleic acid sequence of SEQ ID NO: 16; and
   e) a second AAV ITR sequence comprising the nucleic acid sequence of SEQ ID NO: 13.

32. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 14;
   c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence put forth in any one of SEQ ID NOs: 3-10;
   d) a polyA sequence comprising the nucleic acid sequence of SEQ ID NO: 16; and
   e) a second AAV ITR sequence comprising the nucleic acid sequence of SEQ ID NO: 13.

33. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 20;
   c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence put forth in any one of SEQ ID NOs: 3-10;
   d) a polyA sequence comprising the nucleic acid sequence of SEQ ID NO: 21; and
   e) a second AAV ITR sequence comprising the nucleic acid sequence of SEQ ID NO: 13.

34. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 20;
   c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 10;
   d) a polyA sequence comprising the nucleic acid sequence of SEQ ID NO: 21; and
   e) a second AAV ITR sequence comprising the nucleic acid sequence of SEQ ID NO: 13.

35. An rAAV vector of any one of the preceding embodiments, comprising, in the 5' to 3' direction
   a) a first AAV ITR sequence comprising the nucleic acid sequence of SEQ ID NO: 12;
   b) a promoter sequence comprising the nucleic acid sequence of SEQ ID NO: 20;
   c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 6;
d) a polyA sequence comprising the nucleic acid sequence of SEQ ID NO: 21; and
e) a second AAV ITR sequence comprising the nucleic acid sequence of SEQ ID NO: 13.

36. An rAAV vector of any one of the preceding embodiments, comprising, in the 5' to 3' direction
a) a first AAV ITR sequence comprising the nucleic acid sequence of SEQ ID NO: 12;
b) a promoter sequence comprising the nucleic acid sequence of SEQ ID NO: 20;
c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 5;
d) a polyA sequence comprising the nucleic acid sequence of SEQ ID NO: 21; and
e) a second AAV ITR sequence comprising the nucleic acid sequence of SEQ ID NO: 13.

37. An rAAV vector of any one of the preceding embodiments, comprising, in the 5' to 3' direction
a) a first AAV ITR sequence comprising the nucleic acid sequence of SEQ ID NO: 12;
b) a promoter sequence comprising the nucleic acid sequence of SEQ ID NO: 20;
c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 5;
d) a polyA sequence comprising the nucleic acid sequence of SEQ ID NO: 16; and
e) a second AAV ITR sequence comprising the nucleic acid sequence of SEQ ID NO: 13.

38. An rAAV vector of any one of the preceding embodiments, comprising, in the 5' to 3' direction
a) a first AAV ITR sequence comprising the nucleic acid sequence of SEQ ID NO: 12;
b) a promoter sequence comprising the nucleic acid sequence of SEQ ID NO: 20;
c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 3;
d) a polyA sequence comprising the nucleic acid sequence of SEQ ID NO: 21; and
e) a second AAV ITR sequence comprising the nucleic acid sequence of SEQ ID NO: 13.

39. An rAAV vector of any one of the preceding embodiments, comprising, in the 5' to 3' direction
a) a first AAV ITR sequence comprising the nucleic acid sequence of SEQ ID NO: 20;
b) a promoter sequence comprising the nucleic acid sequence of SEQ ID NO: 15;
c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 10;
d) a polyA sequence comprising the nucleic acid sequence of SEQ ID NO: 16; and
e) a second AAV ITR sequence comprising the nucleic acid sequence of SEQ ID NO: 21.

41. An rAAV viral vector comprising:
a) an rAAV vector of any one of the preceding embodiments; and
b) an AAV capsid protein.

42. The rAAV viral vector of embodiment 44, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

43. The rAAV viral vector of embodiment 45, wherein the AAV capsid protein is an AAV1 capsid protein.

44. The rAAV viral vector of embodiment 45, wherein the AAV capsid protein is an AAV2 capsid protein.

45. The rAAV viral vector of embodiment 45, wherein the AAV capsid protein is an AAV3 capsid protein.

4946 The rAAV viral vector of embodiment 45, wherein the AAV capsid protein is an AAV4 capsid protein.

47. The rAAV viral vector of embodiment 45, wherein the AAV capsid protein is an AAV5 capsid protein.

48. The rAAV viral vector of embodiment 45, wherein the AAV capsid protein is an AAV6 capsid protein.

49. The rAAV viral vector of embodiment 45, wherein the AAV capsid protein is an AAV7 capsid protein.

50. The rAAV viral vector of embodiment 45, wherein the AAV capsid protein is an AAV8 capsid protein.

51. The rAAV viral vector of embodiment 45, wherein the AAV capsid protein is an AAV9 capsid protein.

52. The rAAV viral vector of embodiment 45, wherein the AAV capsid protein is an AAV10 capsid protein.

53. The rAAV viral vector of embodiment 45, wherein the AAV capsid protein is an AAV11 capsid protein.

54. The rAAV viral vector of embodiment 45, wherein the AAV capsid protein is an AAV12 capsid protein.

55. The rAAV viral vector of embodiment 45, wherein the AAV capsid protein is an AAV13 capsid protein.

56. The rAAV viral vector of embodiment 45, wherein the AAV capsid protein is an AAVPHP.B capsid protein.

57. The rAAV viral vector of embodiment 45, wherein the AAV capsid protein is an AAVrh74 capsid protein.

58. The rAAV viral vector of embodiment 45, wherein the AAV capsid protein is an AAVrh.10 capsid protein.

Compositions and Pharmaceutical Compositions

The present disclosure provides compositions comprising any of the isolated polynucleotides, rAAV, vectors and/or rAAV viral vectors described herein. In some aspects, the compositions can be pharmaceutical compositions. Accordingly, the present disclosure provides pharmaceutical compositions comprising any of the isolated polynucleotides, rAAV vectors, and/or rAAV viral vectors described herein.

The pharmaceutical composition, as described herein, may be formulated by any methods known or developed in the art of pharmacology, which include but are not limited to contacting the active ingredients (e.g., viral particles or recombinant vectors) with an excipient and/or additive or other accessory ingredient, dividing or packaging the product to a dose unit. The viral particles of this disclosure may be formulated with desirable features, e.g., increased stability, increased cell transfection, sustained or delayed release, biodistributions or tropisms, modulated or enhanced translation of encoded protein in vivo, and the release profile of encoded protein in vivo.

As such, the pharmaceutical composition may further comprise saline, lipidoids, liposomes, lipid nanoparticles, polymers, lipoplexes, core-shell nanoparticles, peptides, proteins, cells transfected with viral vectors (e.g., for transplantation into a subject), nanoparticle mimics or combinations thereof. In some aspects, the pharmaceutical composition is formulated as a nanoparticle. In some aspects, the nanoparticle is a self-assembled nucleic acid nanoparticle.

A pharmaceutical composition in accordance with the present disclosure may be prepared, packaged, and/or sold in bulk, as a single unit dose, and/or as a plurality of single unit doses. The amount of the active ingredient is generally equal to the dosage of the active ingredient which would be administered to a subject and/or a convenient fraction of such a dosage such as, for example, one-half or one-third of such a dosage. The formulations of the invention can include one or more excipients and/or additives, each in an amount that together increases the stability of the viral vector, increases cell transfection or transduction by the viral vector, increases the expression of viral vector encoded protein, and/or alters the release profile of viral vector encoded proteins. In some aspects, the pharmaceutical composition comprises an excipient and/or additives. Non limiting examples of excipients and/or additives include solvents, dispersion media, diluents, or other liquid vehicles, dispersion or suspension aids, surface active agents, isotonic agents, thickening or emulsifying agents, preservatives, or combination thereof.

In some aspects, the pharmaceutical composition comprises a cryoprotectant. The term "cryoprotectant" refers to an agent capable of reducing or eliminating damage to a substance during freezing. Non-limiting examples of cryoprotectants include sucrose, trehalose, lactose, glycerol, dextrose, raffinose and/or mannitol.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

In some aspects, a pharmaceutical composition of the present disclosure can comprise phosphate-buffered saline, D-sorbitol, sodium chloride, pluronic F-68 or any combination thereof.

In some aspects, a pharmaceutical composition can comprise sodium chloride, wherein the sodium chloride is present at a concentration of about 100 mM to about 500 mM, or about 200 mM to about 400 mM, or about 300 mM to about 400 mM. In some aspects, the sodium chloride can be present at a concentration of about 350 mM.

In some aspects, a pharmaceutical composition can comprise D-sorbitol, wherein the D-sorbitol is present at a concentration of about 1% to about 10%, or about 2.5% to about 7.5%. In some aspects, the D-sorbitol can be present at a concentration of about 5%.

In some aspects, a pharmaceutical composition can comprise pluronic F-68, wherein the pluronic F-68 is present at a concentration of about 0.00001% to about 0.01%, or about 0.0005% to about 0.005%. In some aspects, the pluronic F-68 can be present at a concentration of about 0.001%.

Thus, the present disclosure provides a pharmaceutical composition comprising an rAAV vector and/or rAAV viral vector of the present disclosure in a phosphate-buffered saline solution, wherein the pharmaceutical composition further comprises sodium chloride at a concentration of 350 mM, D-sorbitol at a concentration of 5% and pluronic F-68 at a concentration of 0.001%.

Thus, the present disclosure provides a pharmaceutical composition comprising an rAAV vector and/or rAAV viral vector of the present disclosure, wherein the pharmaceutical composition further comprises sodium chloride at a concentration of 350 mM, D-sorbitol at a concentration of 5% and pluronic F-68 at a concentration of 0.001%.

Thus, the present disclosure provides a pharmaceutical composition comprising an rAAV vector and/or rAAV viral vector of the present disclosure in a phosphate-buffered saline solution, wherein the pharmaceutical composition further comprises sodium chloride at a concentration of 350 mM, D-sorbitol at a concentration of 5%.

Thus, the present disclosure provides a pharmaceutical composition comprising an rAAV vector and/or rAAV viral vector of the present disclosure, wherein the pharmaceutical composition further comprises sodium chloride at a concentration of 350 mM, D-sorbitol at a concentration of 5%.

Methods of Using the Compositions of the Disclosure

The present disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In one aspect, the subject is a mammal. Preferably, the subject is human. The terms "subject" and "patient" are used interchangeably herein.

This disclosure provides methods of preventing or treating a disorder, comprising, consisting essentially of, or consisting of administering to a subject a therapeutically effective amount of any one of the pharmaceutical compositions disclosed herein.

In some aspects, the disease can be a genetic disorder involving a SURF1 gene.

In some aspects, the disclosure provides methods of preventing or treating SURF1 deficiency, Leigh Syndrome, Mitochondrial complex IV deficiency or Charcot-Marie-Tooth disease 4K.

In some aspects, a disease can be a disease that is characterized by the loss-of-function of at least one copy of the SURF1 gene in the genome of a subject. In some aspects, a disease can be a disease that is characterized by a decrease in function of at least one copy of a SURF1 gene in the genome of a subject. In some aspects, a disease can be a disease that is characterized by at least one mutation in at least one mutation in at least one copy of a SURF1 gene in the genome of the subject.

A mutation in a SURF1 gene can be any type of mutation that is known in the art. Non-limiting examples of mutations include somatic mutations, single nucleotide variants (SNVs), nonsense mutations, insertions, deletions, duplications, frameshift mutations, repeat expansions, short insertions and deletions (INDELs), long INDELs, alternative splicing, the products of alternative splicing, altered initiation of translation, the products of altered initiation of translation, proteomic cleavage, and the products of proteomic cleavage.

In some aspects, a disease can be a disease that is characterized by a decrease in expression of a SURF1 gene in a subject as compared to a control subject that does not have the disease. In some aspects, the decrease in expression can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the amount of SURF1 in a subject as compared to a control subject that does not have the disease. In some aspects, the decrease in the amount of SURF1 can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

In some aspects, a disease can be a disease that is characterized by a decrease in the activity of SURF1 in a subject as compared to a control subject that does not have the disease. In some aspects, the decrease in the activity of SURF1 can be at least about 10%, or at least about 20%, or at least about 30%, or at least about 40%, or at least about 50%, or at least about 60%, or at least about 70%, or at least about 80%, or at least about 90%, or at least about 95%, or at least about 99%, or at least about 100%.

A subject to be treated using the methods, compositions, pharmaceutical compositions, rAAV vectors or rAAV viral vectors of the present disclosure can have any of the diseases and/or symptoms described herein.

In some aspects, a subject can be less than 0.5 years of age, or less than 1 year of age, or less than 1.5 years of age, or less than 2 years of age, or at less than 2.5 years of age, or less than 3 years of age, or less than 3.5 years of age, or less than 3.5 years of age, or less than 4 years of age, or less than 4.5 years of age, or less than 5 years of age, or less than 5.5 years of age, or less than 6 years of age, or less than 6.5 years of age, or less than 7 years of age, or less than 7.5 years of age, or less than 8 years of age, or less than 8.5 years of age, or less than 9 years of age, or less than 9.5 years of age, or less than 10 years of age. In some aspects the subject can be less than 11 years of age, less than 12 years of age, less than 13 years of age, less than 14 years of age, less than 15 years of age, less than 20 years of age, less than 30 years of age, less than 40 years of age, less than 50 years of age, less than 60 years of age, less than 70 years of age, less than 80 years of age, less than 90 years of age, less than 100 years of age, less than 110 years of age, or less than 120 years of age. In some aspects, a subject can be less than 0.5 years of age. In some aspects, a subject can be less than 4 years of age. In some aspects, a subject can be less than 10 years of age.

The methods of treatment and prevention disclosed herein may be combined with appropriate diagnostic techniques to identify and select patients for the therapy or prevention.

The disclosure provides methods of increasing the level of a protein in a host cell, comprising contacting the host cell with any one of the rAAV viral vectors disclosed herein, wherein the rAAV viral vectors comprises any one of the rAAV vectors disclosed herein, comprising a transgene nucleic acid molecule encoding the protein. In some aspects, the protein is a therapeutic protein. In some aspects, the host cell is in vitro, in vivo, or ex vivo. In some aspects, the host cell is derived from a subject. In some aspects, the subject suffers from a disorder, which results in a reduced level and/or functionality of the protein, as compared to the level and/or functionality of the protein in a normal subject.

In some aspects, the level of the protein is increased to level of about $1\times10^{-7}$ ng, about $3\times10^{-7}$ ng, about $5\times10^{-7}$ ng, about $7\times10^{-7}$ ng, about $9\times10^{-7}$ ng, about $1\times10^{-6}$ ng, about $2\times10^{-6}$ ng, about $3\times10^{-6}$ ng, about $4\times10^{-6}$ ng, about $6\times10^{-6}$ ng, about $7\times10^{-6}$ ng, about $8\times10^{-6}$ ng, about $9\times10^{-6}$ ng, about $10\times10^{-6}$ ng, about $12\times10^{-6}$ ng, about $14\times10^{-6}$ ng, about $16\times10^{-6}$ ng, about $18\times10^{-6}$ ng, about $20\times10^{-6}$ ng, about $25\times10^{-6}$ ng, about $30\times10^{-6}$ ng, about $35\times10^{-6}$ ng, about $40\times10^{-6}$ ng, about $45\times10^{-6}$ ng, about $50\times10^{-6}$ ng, about $55\times10^{-6}$ ng, about $60\times10^{-6}$ ng, about $65\times10^{-6}$ ng, about $70\times10^{-6}$ ng, about $75\times10^{-6}$ ng, about $80\times10^{-6}$ ng, about $85\times10^{-6}$ ng, about $90\times10^{-6}$ ng, about $95\times10^{-6}$ ng, about $10\times10^{-5}$ ng, about $20\times10^{-5}$ ng, about $30\times10^{-5}$ ng, about $40\times10^{-5}$ ng, about $50\times10^{-5}$ ng, about $60\times10^{-5}$ ng, about $70\times10^{-5}$ ng, about $80\times10^{-5}$ ng, or about $90\times10^{-5}$ ng in the host cell.

The disclosure provides methods of introducing a gene of interest to a cell in a subject comprising contacting the cell with an effective amount of any one of the rAAV viral vectors disclosed herein, wherein the rAAV viral vectors contain any one of the rAAV vectors disclosed herein, comprising the gene of interest.

In some aspects of the methods of the present disclosure, a subject can also be administered a prophylactic immunosuppressant treatment regimen in addition to being administered an rAAV vector or rAAV viral vector of the present disclosure. In some aspects, an immunosuppressant treatment regimen can comprise administering at least one immunosuppressive therapeutic. Non limiting examples of immunosuppressive therapeutics include, but are not limited to, Sirolimus (rapamycin), acetaminophen, diphenhydramine, IV methylprednisolone, prednisone, or any combination thereof. An immunosuppressive therapeutic can be administered prior to the day of administration of the rAAV vector and/or rAAV viral vector, on the same day as the administration of the rAAV vector and/or rAAV viral vector, or any day following the administration of the rAAV vector and/or rAAV viral vector.

A "subject" of diagnosis or treatment is a cell or an animal such as a mammal, or a human. A subject is not limited to a specific species and includes non-human animals subject to diagnosis or treatment and those subject to infections or animal models, including, without limitation, simian, murine, rat, canine, or leporid species, as well as other livestock, sport animals, or pets. In some aspects, the subject is a human.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein the term "effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, the effective amount can be the amount sufficient to result in regaining part or full function of a gene that is deficient in a subject. In some aspects, the effective amount of an rAAV viral vector is the amount sufficient to result in expression of a gene in a subject such that SURF1 is produced. In some aspects, the effective amount is the amount required to increase galactose metabolism in a subject in need thereof. The skilled artisan will be able to determine appropriate amounts depending on these and other factors.

In some aspects, the effective amount will depend on the size and nature of the application in question. It will also depend on the nature and sensitivity of the target subject and the methods in use. The skilled artisan will be able to determine the effective amount based on these and other considerations. The effective amount may comprise, consist essentially of, or consist of one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and other animals, treating veterinarian.

Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. It is noted that dosage may be impacted by the route of administration. Suitable dosage formulations and methods of administering the agents are known in the art. Non-limiting examples of such suitable dosages may be as low as $10^9$ vector genomes to as much as $10^{17}$ vector genomes per administration.

In some aspects of the methods described herein, the number of vector particles (e.g., rAAV viral vectors) administered to the subject ranges from about $10^9$ to about $10^{17}$. In some aspects, about $10^{10}$ to about $10^{12}$, about $10^{11}$ to about $10^{13}$, about $10^{11}$ to about $10^{12}$, about $10^{11}$ to about $10^{14}$, about $10^{12}$ to about $10^{16}$, about $10^{13}$ to about $10^{16}$, about $10^{14}$ to about $10^{15}$, about $5\times10^{11}$ to about $5\times10^{12}$, or about $10^{12}$ to about $10^{13}$ viral particles are administered to the subject.

In some aspects of the methods described herein, the number of viral particles (e.g., rAAV viral vectors) administered to the subject is at least about $10^{10}$, or at least about $10^{11}$, or at least about $10^{12}$, or at least about $10^{13}$, or at least about $10^{14}$, or at least about $10^{15}$, or at least about $10^{16}$, or at least about $10^{17}$ viral particles.

In some aspects of the methods described herein, the number of viral particles (e.g., rAAV viral vectors) administered to the subject can depend on the age of the subject. In non-limiting examples, a subject that is 7 years of age or older can be administered about $10\times10^{14}$ viral particles, a subject that is about 4 years of age to about 7 years of age can be administered about $10\times10^{14}$ viral particles, a subject that is about 3 years of age to about 4 years of age can be administered about $9\times10^{14}$ viral particles, a subject that is about 2 years of age to about 3 years of age can be about $8.2\times10^{14}$ viral particles, a subject that is about 1 year of age to about 2 years of age can be administered about $7.3\times10^{14}$ viral particles, a subject that is about 0.5 years of age to about 1 year of age can be administered about $4\times10^{14}$ viral particles, or a subject that is less than 0.5 years of age can be administered $3\times10^{14}$ viral particles.

In some aspects, the amounts of viral particles in a composition, pharmaceutical composition, or the amount of viral particles administered to a patient can calculated based on the percentage of viral particles that are predicted to contain viral genomes.

In some aspects, rAAV viral vectors of the present disclosure can be introduced to the subject intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally; such introduction may also be intra-arterial, intracardiac, subventricular, epidural, intracerebral, intracerebroventricular, sub-retinal, intravitreal, intraarticular, intraperitoneal, intrauterine, or any combination thereof. In some aspects, the viral particles are delivered to a desired target tissue, e.g., to the lung, eye, or CNS, as non-limiting examples. In some aspects, delivery of viral particles is systemic. The intracisternal route of administration involves administration of a drug directly into the cerebrospinal fluid of the brain ventricles. It could be performed by direct injection into the cisterna magna or via a permanently positioned tube. In some aspects, the rAAV viral vectors of the present disclosure are administered intrathecally.

In some aspects, the rAAV viral vectors of the present disclosure repair a gene deficiency in a subject. In some aspects, the ratio of repaired target polynucleotide or polypeptide to unrepaired target polynucleotide or polypeptide in a successfully treated cell, tissue, organ or subject is at least about 1.5:1, about 2:1, about 3:1, about 4:1, about 5:1, about 6:1, about 7:1, about 8:1, about 9:1, about 10:1, about 20:1, about 50:1, about 100:1, about 1000:1, about 10,000:1, about 100,000:1, or about 1,000,000:1. The amount or ratio of repaired target polynucleotide or polypeptide can be determined by any method known in the art, including but not limited to western blot, northern blot, Southern blot, PCR, sequencing, mass spectrometry, flow cytometry, immunohistochemistry, immunofluorescence, fluorescence in situ hybridization, next generation sequencing, immunoblot, and ELISA.

Administration of the rAAV vectors, rAAV viral vectors, compositions or pharmaceutical compositions of this disclosure can be effected in one dose, continuously or intermittently throughout the course of treatment. In some aspects, the rAAV vectors, rAAV viral vectors, compositions, or pharmaceutical compositions of this disclosure are parenterally administered by injection, infusion, or implantation.

In some aspects, the rAAV viral vectors of this disclosure show enhanced tropism for brain and cervical spine. In some aspects, the rAAV viral vectors of the disclosure can cross the blood-brain-barrier (BBB).

Methods of Manufacture

A variety of approaches may be used to produce rAAV viral vectors of the present disclosure. In some aspects, packaging is achieved by using a helper virus or helper plasmid and a cell line. The helper virus or helper plasmid contains elements and sequences that facilitate viral vector production. In another aspect, the helper plasmid is stably incorporated into the genome of a packaging cell line, such that the packaging cell line does not require additional transfection with a helper plasmid.

In some aspects, the cell is a packaging or helper cell line. In some aspects, the helper cell line is eukaryotic cell; for example, an HEK 293 cell or 293T cell. In some aspects, the helper cell is a yeast cell or an insect cell.

In some aspects, the cell comprises a nucleic acid encoding a tetracycline activator protein; and a promoter that regulates expression of the tetracycline activator protein. In some aspects, the promoter that regulates expression of the tetracycline activator protein is a constitutive promoter. In some aspects, the promoter is a phosphoglycerate kinase promoter (PGK) or a CMV promoter.

A helper plasmid may comprise, for example, at least one viral helper DNA sequence derived from a replication-incompetent viral genome encoding in trans all virion proteins required to package a replication incompetent AAV, and for producing virion proteins capable of packaging the replication-incompetent AAV at high titer, without the production of replication-competent AAV.

Helper plasmids for packaging AAV are known in the art, see, e.g., U.S. Patent Pub. No. 2004/0235174 A1, incorporated herein by reference. As stated therein, an AAV helper plasmid may contain as helper virus DNA sequences, by way of non-limiting example, the Ad5 genes E2A, E4 and VA, controlled by their respective original promoters or by heterologous promoters. AAV helper plasmids may additionally contain an expression cassette for the expression of a marker protein such as a fluorescent protein to permit the simple detection of transfection of a desired target cell.

The disclosure provides methods of producing rAAV viral vectors comprising transfecting a packaging cell line with any one of the AAV helper plasmids disclosed herein; and any one of the rAAV vectors disclosed herein. In some aspects, the AAV helper plasmid and rAAV vector are co-transfected into the packaging cell line. In some aspects, the cell line is a mammalian cell line, for example, human embryonic kidney (HEK) 293 cell line. The disclosure provides cells comprising any one of the rAAV vectors and/or rAAV viral vectors disclosed herein.

As used herein, the term "helper" in reference to a virus or plasmid refers to a virus or plasmid used to provide the additional components necessary for replication and packaging of any one of the rAAV vectors disclosed herein. The components encoded by a helper virus may include any genes required for virion assembly, encapsidation, genome replication, and/or packaging. For example, the helper virus or plasmid may encode necessary enzymes for the replication of the viral genome. Non-limiting examples of helper viruses and plasmids suitable for use with AAV constructs include pHELP (plasmid), adenovirus (virus), or herpesvirus (virus). In some aspects, the pHELP plasmid may be the pHELPK plasmid, wherein the ampicillin expression cassette is exchanged with a kanamycin expression cassette.

As used herein, a packaging cell (or a helper cell) is a cell used to produce viral vectors. Producing recombinant AAV viral vectors requires Rep and Cap proteins provided in trans as well as gene sequences from Adenovirus that help AAV replicate. In some aspects, Packaging/helper cells contain a plasmid is stably incorporated into the genome of the cell. In other aspects, the packaging cell may be transiently transfected. Typically, a packaging cell is a eukaryotic cell, such as a mammalian cell or an insect cell.

Kits

The isolated polynucleotides, rAAV vectors, rAAV viral vectors, compositions, and/or pharmaceutical compositions described herein may be assembled into pharmaceutical or diagnostic or research kits to facilitate their use in therapeutic, diagnostic, or research applications. In some aspects, the kits of the present disclosure include any one of the isolated polynucleotides, rAAV vectors, rAAV viral vectors, compositions, pharmaceutical compositions, host cells, isolated tissues, as described herein.

In some aspects, a kit further comprises instructions for use. Specifically, such kits may include one or more agents described herein, along with instructions describing the intended application and the proper use of these agents. In some aspects, the kit may include instructions for mixing one or more components of the kit and/or isolating and mixing a sample and applying to a subject. In some aspects, agents in a kit are in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. In some aspects, the compositions may be provided in a preservation solution (e.g., cryopreservation solution). Non-limiting examples of preservation solutions include DMSO, paraformaldehyde, and CryoStor® (Stem Cell Technologies, Vancouver, Canada). In some aspects, the preservation solution contains an amount of metalloprotease inhibitors.

In some aspects, the kit contains any one or more of the components described herein in one or more containers. Thus, in some aspects, the kit may include a container housing agents described herein. The agents may be in the form of a liquid, gel or solid (powder). The agents may be prepared sterilely, packaged in a syringe and shipped refrigerated. Alternatively, they may be housed in a vial or other container for storage. A second container may have other agents prepared sterilely. Alternatively, the kit may include the active agents premixed and shipped in a syringe, vial, tube, or other container. The kit may have one or more or all of the components required to administer the agents to a subject, such as a syringe, topical application devices, or IV needle tubing and bag.

Further Definitions

Unless the context indicates otherwise, it is specifically intended that the various features of the invention described herein can be used in any combination. Moreover, the disclosure also contemplates that, in some aspects, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless explicitly indicated otherwise, all specified aspects, embodiments, features, and terms intend to include both the recited aspect, embodiment, feature, or term and biological equivalents thereof.

The practice of the present technology will employ, unless otherwise indicated, conventional techniques of organic chemistry, pharmacology, immunology, molecular biology, microbiology, cell biology and recombinant DNA, which are within the skill of the art. See, e.g., Sambrook, Fritsch and Maniatis, Molecular Cloning: A Laboratory Manual, 2nd edition (1989); Current Protocols In Molecular Biology (F. M. Ausubel, et al. eds., (1987)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, a Laboratory Manual, and Animal Cell Culture (R I. Freshney, ed. (1987)).

As used herein, the term "comprising" is intended to mean that the compositions and methods include the recited elements, but do not exclude others. As used herein, the transitional phrase "consisting essentially of" (and grammatical variants) is to be interpreted as encompassing the recited materials or steps and those that do not materially affect the basic and novel characteristic(s) of the recited embodiment. Thus, the term "consisting essentially of" as used herein should not be interpreted as equivalent to "comprising." "Consisting of" shall mean excluding more than trace elements of other ingredients and substantial method steps for administering the compositions disclosed herein. Aspects defined by each of these transition terms are within the scope of the present disclosure. Any of the terms "comprising," "consisting essentially of," and "consisting of" can be replaced with either of the other two terms, while retaining their ordinary meanings.

All numerical designations, e.g., pH, temperature, time, concentration, and molecular weight, including ranges, are approximations which are varied (+) or (−) by increments of 1.0 or 0.1, as appropriate, or, alternatively, by a variation of +/−15%, 10%, 5%, 2%. It is to be understood, although not always explicitly stated, that all numerical designations are preceded by the term "about". It also is to be understood, although not always explicitly stated, that the reagents described herein are merely exemplary and that equivalents of such are known in the art. The term "about," as used herein when referring to a measurable value such as an amount or concentration and the like, is meant to encompass variations of 20%, 10%, 5%, 1%, 0.5%, or even 0.1% of the specified amount.

The terms "acceptable," "effective," or "sufficient" when used to describe the selection of any components, ranges, dose forms, etc. disclosed herein intend that said component, range, dose form, etc. is suitable for the disclosed purpose.

Also, as used herein, "and/or" refers to and encompasses any and all possible combinations of one or more of the associated listed items, as well as the lack of combinations when interpreted in the alternative ("or").

Unless specifically recited, the term "host cell" includes a eukaryotic host cell, including, for example, fungal cells, yeast cells, higher plant cells, insect cells and mammalian cells. Non-limiting examples of eukaryotic host cells include simian, bovine, porcine, murine, rat, avian, reptilian and human, e.g., HEK293 cells and 293T cells.

The term "isolated" as used herein refers to molecules or biologicals or cellular materials being substantially free from other materials.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising, consisting essentially of, or consisting of purine and pyrimidine bases or other natural, chemically or biochemically modified, non-natural, or derivatized nucleotide bases.

A "gene" refers to a polynucleotide containing at least one open reading frame (ORF) that is capable of encoding a particular polypeptide or protein. A "gene product" or, alternatively, a "gene expression product" refers to the amino acid sequence (e.g., peptide or polypeptide) generated when a gene is transcribed and translated.

As used herein, "expression" refers to the two-step process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell.

"Under transcriptional control" is a term well understood in the art and indicates that transcription of a polynucleotide sequence, usually a DNA sequence, depends on its being operatively linked to an element that contributes to the initiation of, or promotes, transcription. "Operatively linked" intends that the polynucleotides are arranged in a manner that allows them to function in a cell. In one aspect, these promoters can be operatively linked to the downstream sequences.

The term "protein", "peptide" and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise, consist essentially of, or consist of a protein's or peptide's sequence. As used herein the term "amino acid" refers to either natural and/or unnatural or synthetic amino acids, including glycine and both the D and L optical isomers, amino acid analogs and peptidomimetics.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some aspects, the signal peptide is removed following localization. Examples of signal peptides are well known in the art. Non-limiting examples are those described in U.S. Pat. Nos. 8,853,381, 5,958,736, and 8,795,965. In some aspects, the signal peptide can be an IDUA signal peptide.

The terms "equivalent" or "biological equivalent" are used interchangeably when referring to a particular molecule, biological material, or cellular material and intend those having minimal homology while still maintaining desired structure or functionality. Non-limiting examples of equivalent polypeptides include a polypeptide having at least about 60%, at least about 65%, at least about 70%, at least about 75%, at least about 80%, at least about 85%, at least about 90%, at least about 95% identity or at least about 99% identity to a reference polypeptide (for instance, a wild-type polypeptide); or a polypeptide which is encoded by a polynucleotide having at least about 70%, at least about 75%, at least about 80%, at least about 85%, at least about 90%, at least about 95% identity, at least about 97% sequence identity or at least about 99% sequence identity to the reference polynucleotide (for instance, a wild-type polynucleotide).

"Homology" or "identity" or "similarity" refers to sequence similarity between two peptides or between two nucleic acid molecules. Percent identity can be determined by comparing a position in each sequence that may be aligned for purposes of comparison. When a position in the compared sequence is occupied by the same base or amino acid, then the molecules are identical at that position. A degree of identity between sequences is a function of the number of matching positions shared by the sequences. "Unrelated" or "non-homologous" sequences share less than 40% identity, less than 25% identity, with one of the sequences of the present disclosure. Alignment and percent sequence identity may be determined for the nucleic acid or amino acid sequences provided herein by importing said nucleic acid or amino acid sequences into and using ClustalW (available at https://genome.jp/tools-bin/clustalw/). For example, the ClustalW parameters used for performing the protein sequence alignments found herein were generated using the Gonnet (for protein) weight matrix. In some aspects, the ClustalW parameters used for performing nucleic acid sequence alignments using the nucleic acid sequences found herein are generated using the ClustalW (for DNA) weight matrix.

As used herein, amino acid modifications may be amino acid substitutions, amino acid deletions or amino acid insertions. Amino acid substitutions may be conservative amino acid substitutions or non-conservative amino acid substitutions. A conservative replacement (also called a conservative mutation, a conservative substitution or a conservative variation) is an amino acid replacement in a protein that changes a given amino acid to a different amino acid with similar biochemical properties (e.g., charge, hydrophobicity or size). As used herein, "conservative variations" refer to the replacement of an amino acid residue by another, biologically similar residue. Examples of conservative variations include the substitution of one hydrophobic residue such as isoleucine, valine, leucine or methionine for another; or the substitution of one charged or polar residue for another, such as the substitution of arginine for lysine, glutamic acid for aspartic acid, glutamine for asparagine, and the like. Other illustrative examples of conservative substitutions include the changes of: alanine to serine; asparagine to glutamine or histidine; aspartate to glutamate; cysteine to serine; glycine to proline; histidine to asparagine or glutamine; lysine to arginine, glutamine, or glutamate; phenylalanine to tyrosine, serine to threonine; threonine to serine; tryptophan to tyrosine; tyrosine to tryptophan or phenylalanine; and the like.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is a DNA molecule that is typically separate from and capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or, alternatively, the proteins produced may act as toxins under similar circumstances. It is known in the art that while plasmid vectors often exist as extrachromosomal circular DNA molecules, plasmid vectors may also be designed to be stably integrated into a host chromosome either randomly or in a targeted manner, and such integration may be accomplished using either a circular plasmid or a plasmid that has been linearized prior to introduction into the host cell.

"Plasmids" used in genetic engineering are called "plasmid vectors". Many plasmids are commercially available for such uses. The gene to be replicated is inserted into copies of a plasmid containing genes that make cells resistant to particular antibiotics, and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria or eukaryotic cells containing a plasmid harboring the gene of interest, which can be induced to produce large amounts of proteins from the inserted gene.

In aspects where gene transfer is mediated by a DNA viral vector, such as an adenovirus (Ad) or adeno-associated virus (AAV), a vector construct refers to the polynucleotide comprising, consisting essentially of, or consisting of the viral genome or part thereof, and a transgene.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected), or a group of tissues making up an organ or part or region of the body of an organism. The tissue may comprise, consist essentially of, or consist of a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

EXAMPLES

Example 1: Codon Optimization of a SURF1 Transgene

A transgene nucleic acid molecule comprising a codon optimized nucleic acid sequence encoding a SURF1 polypeptide was designed. The SURF1 transgene sequence was codon optimized to facilitate the ease of transgene detection by molecular methods, and minimize rare unrelated transcripts or aberrant splicing variants. The SURF1 transgene sequence was codon optimized to remove rare codons, cryptic splice sites, and cryptic start sites with an altered nucleic acid sequence that still encodes the fully WT protein. The purpose of the codon optimization was to enable easier tracking of the vector sequence to distinguish it from the endogenous chromosomal gene sequence. Molecular methods such as polymerase chain reaction, Southern blot, Northern blot, in situ hybridization, etc. can thus be used to readily detect the distribution of the vector transgene and expressed transgene mRNA in cells, tissues, or body fluids. These changes may also increase expression, and may also reduce expression of alternative proteins that could be immunogenic or otherwise detrimental compared to the natural unmodified gene sequence.

Figure 2:
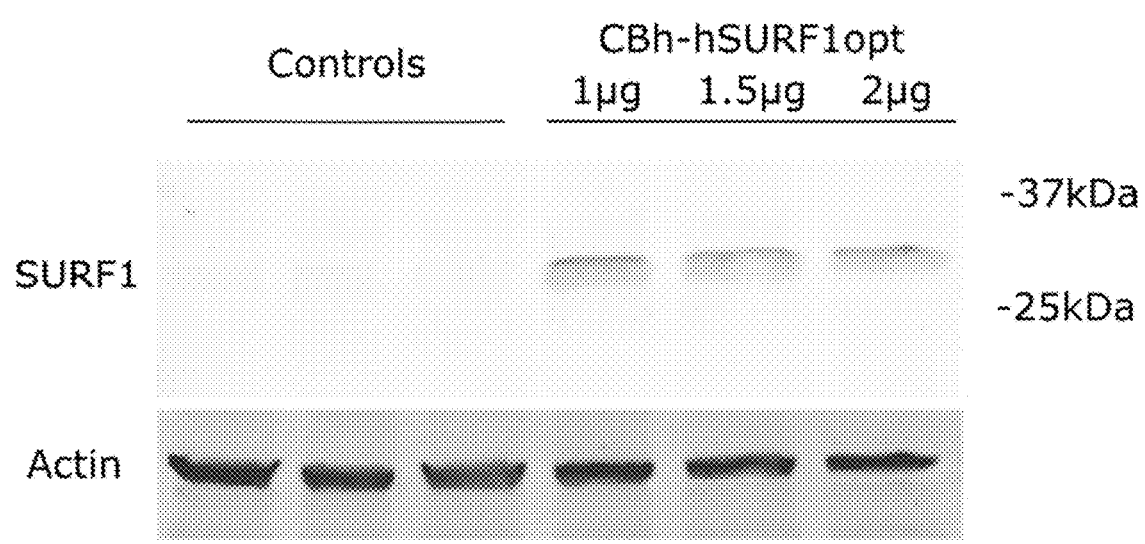
FIG. 2 is a western blot depicting hSURF1 expression in HEK293 cells transfected with the CBh-hSURF1opt plasmid comprising a codon optimized SURF1 sequence.

The expression of hSURF1opt is controlled by hybrid chicken beta actin (CBA) promoter (CBh) and BGH poly (A) tail (AAV9/SURF1). The CBh promoter was used to ensure universal expression of hSURF1opt, which mimic the characteristics of endogenous SURF1. The ability of the hSURF1opt transgene to express hSURF1 protein was demonstrated by transfecting the plasmid into HEK293 cells, as shown in FIG. 2.

Figure 3:
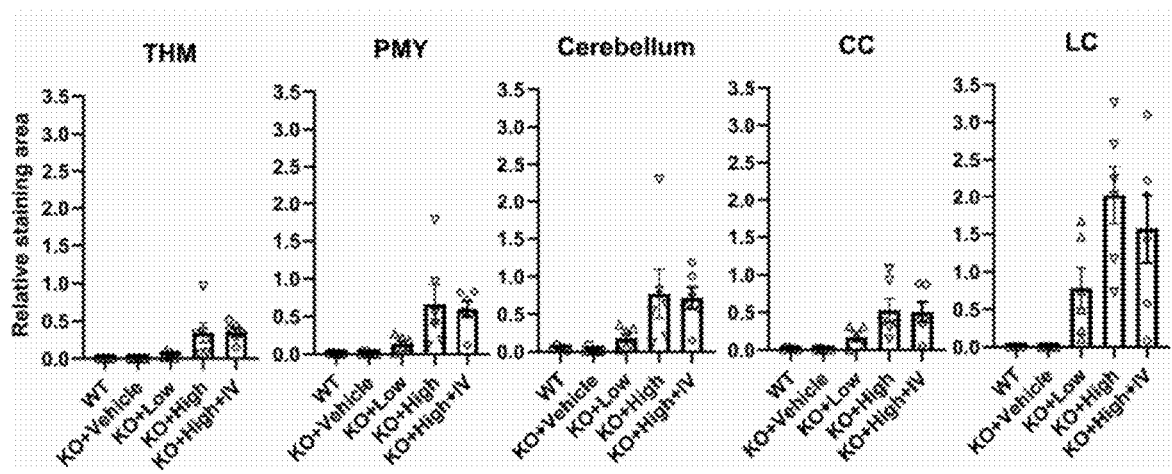
FIG. 3 is a series of graphs depicting expression of SURF1 mRNA in multiple brain areas and the spinal cord of mice treated with AAV9 viral vectors comprising a codon optimized SURF1 nucleic acid sequence (AAV9/hSURF1). THM: thalamus, hypothalamus, and midbrain; PMY: pon and medulla; CC: cervical spinal cord; LC: lumbar spinal cord, Low: low IT dose, High: high IT dose, High+IV: combination intrathecal and intravenous dose.

Example 2: Intrathecal (IT) Delivery of AAV9/hSURF1opt Results in SURF1 Expression in Various Brain Regions and Spinal Cord RNAscope was used to specifically detect mRNA of the hSURF1opt transgene in AAV9/hSURF1-treated mice. Brain and spinal cord were collected from SURF1 KO mice 4-weeks post AAV9/hSURF1 treatment. The expression level of hSURF1opt mRNA in each experimental group was analyzed and is shown in FIG. 3. Percent area staining positive for hSURF1opt mRNA by tissue region (n=6 per group). THM: thalamus, hypothalamus, and midbrain; PMY: pon and medulla; CC: cervical spinal cord; LC: lumbar spinal cord, Low: low IT dose, High: high IT dose, High+IV: combination intrathecal and intravenous dose. Each data point represents measurement from an individual animal, with bars representing the mean±SEM.

The results show that SURF1 mRNA was successfully expressed in all disease-relevant brain areas, cervical spinal cord (furthest from the injection site) and lumbar spinal cord (closest to the injection site). The IT+IV combo treatment did not show significant improvement compared with IT only treatment group.

Example 3: Intrathecal Delivery of AAV9/hSURF1opt Rescues COX Deficiency

Figure 4A:
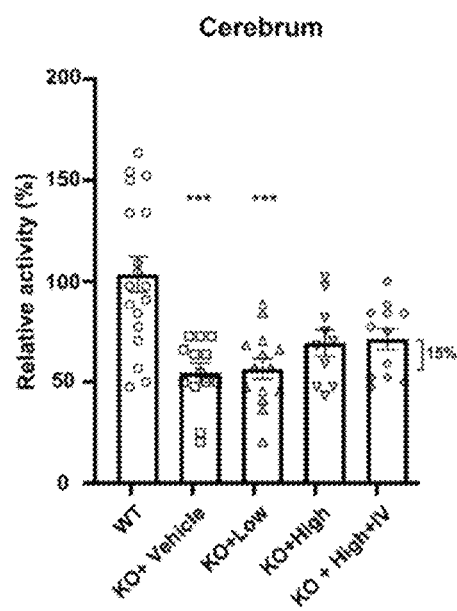
FIG. 4A is a series of graphs depicting partially restored COX activity deficiency in multiple tissues of SURF1 knockout mice upon treatment with AAV9 viral vectors comprising a codon optimized SURF1 nucleic acid sequence.
Figure 4B:
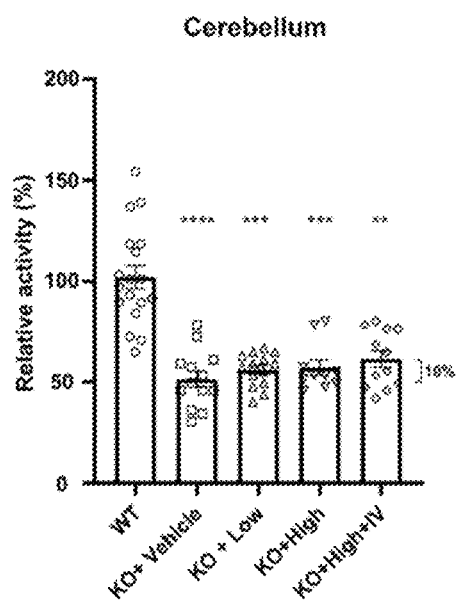
FIG. 4B depicts cerebellum (n=10-18 per group) of WT and SURF1 KO mice with assigned treatments. FIG.
Figure 4C:
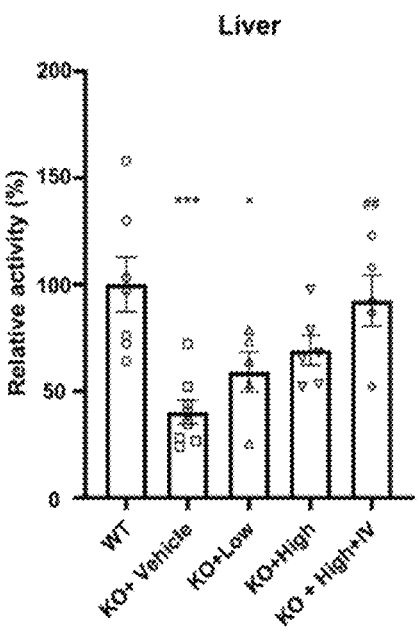
FIG. 4D depicts muscle (n=10-14 per group) of WT and SURF1 KO mice with assigned treatments.
Figure 4D:
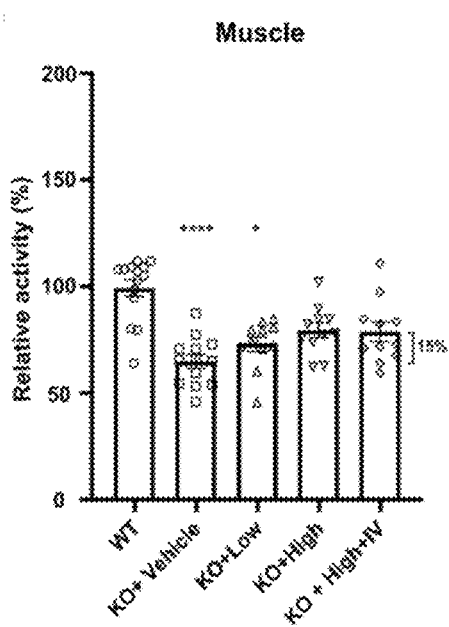

Cytochrome C Oxidase (COX) activity was measured in brain (cerebrum and cerebellum), liver and muscle of AAV9/hSURF1opt treated SURF1 KO mice, and cerebellum and cerebrum were tested separately. As shown in FIG. 4, COX activity of SURF1 KO mice was reduced between 30-60% in all tissues tested compared with that of WT mice. FIG. 4A depicts COX activity of cerebrum (n=10-18 per group), FIG. 4B depicts cerebellum (n=10-18 per group), FIG. 4C depicts liver (n=5-8 per group), and FIG. 4D depicts muscle (n=10-14 per group) of WT and SURF1 KO mice with assigned treatments. All data were normalized to the average of WT mice. Each data point represents measurement from an individual animal, with bars representing the mean±SEM. $*p<0.05$, $p<0.01$, $*p<0.001$, $*p<0.0001$ compared with WT mice. $\#\#p<0.01$ compared with KO+Vehicle mice.

AAV9/hSURF1 administered through IT partially but significantly restored COX activity, and the effect increased with dose escalation.

Figure 5A:
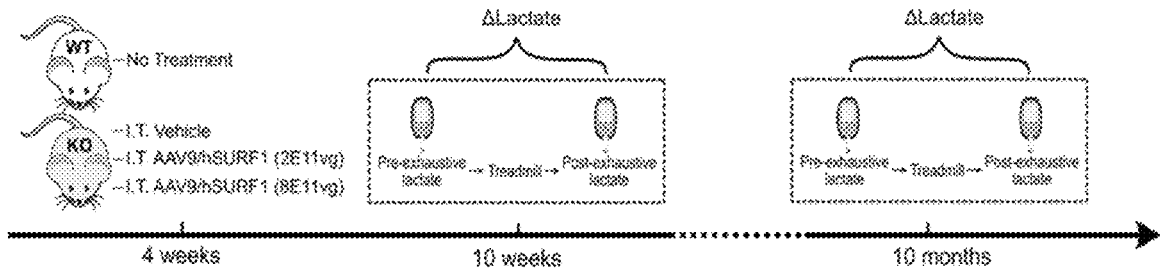
FIG. 5A is a schematic depicting the treatment protocol of impact of AAV9/hSURF1 treatment on serum lactate levels in SURF1 KO mice.
Figure 5B:
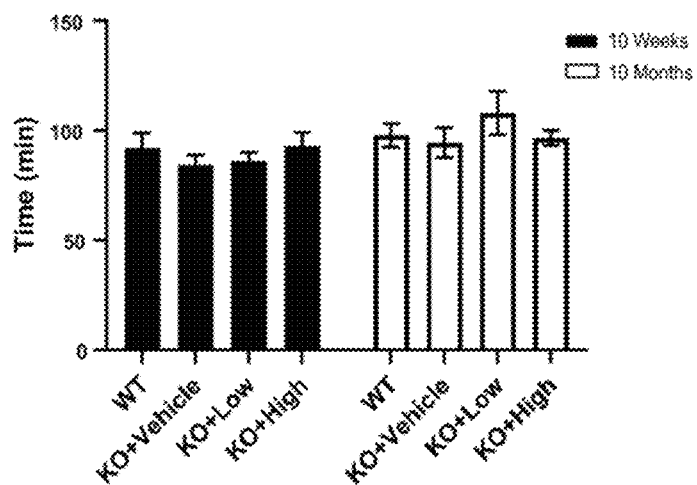
FIG. 5B is a graph depicting differences in running time in mice among groups at both 10-weeks-old and 10-months-old.
Figure 5C:
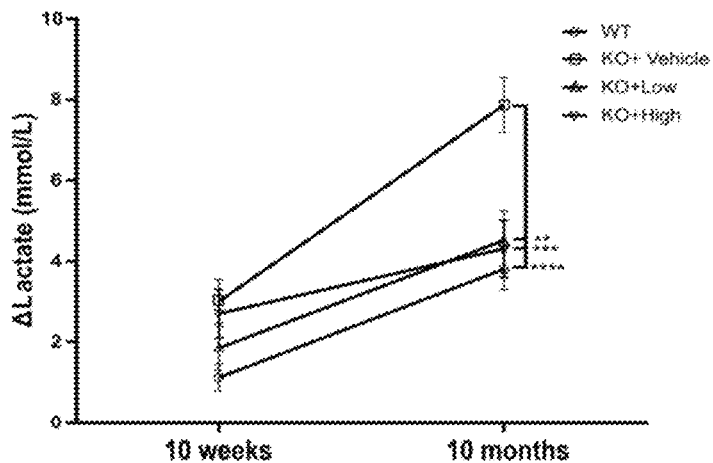
FIG. 5C is a graph depicting change of lactate (ΔLactate) after exercise in mice among groups at both 10-weeks-old and 10-months-old.

Example 4: Intrathecal Delivery of AAV9/hSURF1 Ablated Exhaustive Exercise-Induced Lactic Acidosis in Aged SURF1 KO Mice Serum lactate is increased in SURF1 KO mice and human patients, which is associated with mitochondrial dysfunction. The impact of AAV9/hSURF1 treatment on serum lactate levels was assessed in SURF1 KO mice. The study scheme was shown in FIG. 5A. The mice were tested at two ages, 10 weeks, which is 6 weeks after AAV treatment, and 10 months. SURF1 KO mice do not show lactic acidosis under resting state, but their serum lactate was significantly increased after exhaustive exercise. Thus, the change of lactate (ΔLactate) was measured after exhaustion from treadmill running. As shown in FIG. 5B, there was no differences in their running time among groups at both 10-weeks-old and 10-months-old, suggesting SURF1 KO mice were able to maintain normal endurance capacity even with deficient COX. However, as shown in FIG. 5C, their lactate was increased after the exercise at both ages, while the increment at 10 months old was more significant. FIG. 5B depicts running time on treadmill until exhaustion. FIG. 5C depicts ΔLactate (post-exhaustion lactate-pre-exhaustion lactate) of mice from all tested groups at 10 weeks and 10 months old. Data shown as mean±SEM. $p<0.01$, $*p<0.001$, and $****p<0.0001$ analyzed using two-way ANOVA with Sidak's multiple comparisons test. $\#p<0.05$, $\#\#\#p<0.001$ analyzed using paired t-test.

Low and high dose AAV9/hSURF1 treatment ablated the exhaustive exercise-induced lactic acidosis, suggesting that the gene replacement therapy significantly improved the mitochondrial metabolic functions.

What is claimed is:

1. A recombinant adeno-associated virus (rAAV) vector comprising in 5' to 3' direction,
   (a) a first AAV inverted terminal repeat (ITR) sequence;
   (b) a promoter sequence;
   (c) a transgene nucleic acid molecule comprising a nucleic acid sequence comprising at least 85% identity to SEQ ID NO: 9,
   (d) a poly A sequence; and
   (e) a second AAV ITR sequence.

2. The rAAV vector of claim 1, wherein the SURF1 polypeptide comprises amino acid sequence of SEQ ID NO: 2.

3. The rAAV vector of claim 1, wherein the transgene nucleic acid molecule comprises a nucleic acid sequence comprising at least 95% identity to SEQ ID NO: 9.

4. The rAAV vector of claim 3, wherein the codon optimized transgene nucleic acid molecule comprises a nucleic acid sequence of SEQ ID NO: 9.

5. The rAAV vector of claim 1, wherein the first AAV ITR sequence comprises nucleic acid sequence of SEQ ID NO: 12.

6. The rAAV vector of claim 1, wherein the second AAV ITR sequence nucleic acid sequence of SEQ ID NO 13.

7. The rAAV vector of claim 1, wherein the promoter comprises a JET promoter, a Rous sarcoma virus (RSV) LTR promoter (optionally with the RSV enhancer), a cytomegalovirus (CMV) promoter, an SV40 promoter, a dihydrofolate reductase promoter, a beta-actin promoter, a phosphoglycerol kinase (PGK) promoter, a U6 promoter, an H1 promoter, a CAG promoter, a hybrid chicken beta-actin promoter, an MeCP2 promoter, an EF1 promoter, a ubiquitous chicken β-actin hybrid (CBh) promoter, a U1 a promoter, a U1b promoter, an MeCP2 promoter, an MeP418 promoter, an MeP426 promoter, a minimal MeCP2 promoter, a VMD2 promoter, an mRho promoter, EF1a promoter, Ubc promoter, human β-actin promoter, THE promoter, Ac5 promoter, Polyhedrin promoter, CaMKIIa promoter, Gall promoter, TEF1 promoter, GDS promoter, ADH1 promoter, Ubi promoter, or a-1-antitrypsin (hAAT) promoter.

8. The rAAV of claim 1, wherein the promoter sequence comprises a nucleic acid sequence set forth in SEQ ID NO: 20.

9. The rAAV of claim 1, wherein the promoter sequence comprises nucleic acid sequence of SEQ ID NO: 14.

10. The rAAV vector of claim 1, wherein the polyA sequence comprises nucleic acid sequence of SEQ ID NO: 21.

11. An rAAV vector, comprising, in the 5' to 3' direction
a) a first AAV ITR sequence comprising the nucleic acid sequence of SEQ ID NO: 12;
b) a promoter sequence comprising the nucleic acid sequence of SEQ ID NO: 14;
c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence of SEQ ID NO: 9;
d) a polyA sequence comprising the nucleic acid sequence of SEQ ID NO: 21; and
e) a second AAV ITR sequence comprising the nucleic acid sequence of SEQ ID NO: 13.

12. An rAAV vector, comprising, in the 5' to 3' direction
a) a first AAV ITR sequence comprising the nucleic acid sequence set forth in SEQ ID NO: 12;
b) a promoter sequence comprising the nucleic acid sequence set forth in SEQ ID NO: 20;
c) a transgene nucleic acid molecule, wherein the transgene nucleic acid molecule comprises a nucleic acid sequence encoding for a SURF1 polypeptide, wherein the nucleic acid sequence encoding for a SURF1 polypeptide comprises the nucleic acid sequence set forth in SEQ ID NO: 9;
d) a polyA sequence comprising the nucleic acid sequence set forth in SEQ ID NO: 21; and
e) a second AAV ITR sequence comprising the nucleic acid sequence set forth in SEQ ID NO: 13.

13. An rAAV viral vector comprising
(i) an AAV capsid protein; and
(ii) an rAAV vector of claim 1.

14. The rAAV viral vector of claim 13, wherein the AAV capsid protein is an AAV1 capsid protein, an AAV2 capsid protein, an AAV4 capsid protein, an AAV5 capsid protein, an AAV6 capsid protein, an AAV7 capsid protein, an AAV8 capsid protein, an AAV9 capsid protein, an AAV10 capsid protein, an AAV11 capsid protein, an AAV12 capsid protein, an AAV13 capsid protein, an AAVPHP.B capsid protein, an AAVrh74 capsid protein or an AAVrh.10 capsid protein.

15. The rAAV viral vector of claim 13, wherein the AAV capsid protein is an AAV9 capsid protein.

16. A pharmaceutical composition comprising:
a) the rAAV viral vector of claim 1; and
b) at least one pharmaceutically acceptable excipient and/or additive.

17. A method for treating a mammal having a disease and/or disorder involving a SURF1 gene, the method comprising administering to the mammal by intrathecal injection, the rAAV viral vector of claim 1 or the pharmaceutical composition of claim 16, at a dose ranging from about $10^{12}$ vector particles to about $10^{16}$ vector particles,
wherein the disease and/or disorder involving a SURF1 gene is Leigh Syndrome.

18. The method of claim 17, wherein the rAAV viral vector or the pharmaceutical composition is administered to the subject at a dose of about $10^{14}$ vector particles to about $10^{15}$ vector particles.

* * * * *